US008950236B2

(12) United States Patent
Ishii et al.

(10) Patent No.: US 8,950,236 B2
(45) Date of Patent: Feb. 10, 2015

(54) METHODS FOR PROVIDING A SELECTION OF A RECOMMENDED GOLF BALL

(75) Inventors: Hideyuki Ishii, Portland, OR (US); Yasushi Ichikawa, Tualatin, OR (US); Nicholas A. Leech, Beaverton, OR (US); Arthur Molinari, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 185 days.

(21) Appl. No.: 13/591,068

(22) Filed: Aug. 21, 2012

(65) Prior Publication Data

US 2013/0213153 A1 Aug. 22, 2013

Related U.S. Application Data

(60) Provisional application No. 61/526,660, filed on Aug. 23, 2011.

(51) Int. Cl.

| | |
|---|---|
| ***G01N 3/30*** | (2006.01) |
| ***G01N 33/00*** | (2006.01) |
| ***A63B 69/36*** | (2006.01) |

(Continued)

(52) U.S. Cl.

CPC ................ *G01N 33/00* (2013.01); *A63B 69/36* (2013.01); *A63B 69/3658* (2013.01); *A63B 37/0003* (2013.01); *A63B 37/0006* (2013.01); *A63B 37/0033* (2013.01); *A63B 37/0076* (2013.01); *A63B 37/0084* (2013.01); *A63B 37/0096* (2013.01); *A63B 47/008* (2013.01); *A63B 2069/3605* (2013.01)

USPC ........................................................ 73/12.02

(58) Field of Classification Search

CPC ........... A63B 69/3658; A63B 2220/35; A63B 2243/0029; A63B 37/0003

USPC ............................................ 73/12.01, 12.02

See application file for complete search history.

(56) References Cited

U.S. PATENT DOCUMENTS

| | | | | |
|---|---|---|---|---|
| 4,375,887 | A * | 3/1983 | Lynch et al. | 473/409 |
| 5,766,097 | A | 6/1998 | Horiuchi et al. | |
| 5,967,906 | A | 10/1999 | Horiuchi et al. | |

(Continued)

FOREIGN PATENT DOCUMENTS

| | | |
|---|---|---|
| JP | 2002000787 | 1/2002 |
| JP | 2004135706 A | 5/2004 |

(Continued)

OTHER PUBLICATIONS

International Search Report and Written Opinion in PCT Application No. PCT/US2012/051834, mailed on Feb. 25, 2013.

*Primary Examiner* — Hezron E Williams
*Assistant Examiner* — Nashmiya Fayyaz
(74) *Attorney, Agent, or Firm* — Honigman Miller Schwartz and Cohn LLP; Anna M. Budde; Jonathan P. O'Brien

(57) ABSTRACT

Methods for evaluating and providing selections of recommended golf balls, golf ball constructions, and configurations of golf ball construction components are provided. Such methods may involve obtaining or measuring spin measurements against a plurality of golf clubs for each of a plurality of golf balls. A linear relationship may be used to determine a spin slope for each golf ball on the basis of the set of spin measurements associated with that golf ball. In turn, a selection of a recommended golf ball, golf ball construction, or configuration of a ball construction component may be made based upon which golf ball has the larger spin slope.

21 Claims, 14 Drawing Sheets

1200
1050
1060
1000
1220
1230
1050
1060
1100
1210
1240
1220

(51) Int. Cl.
*A63B 37/00* (2006.01)
*A63B 47/00* (2006.01)

(56) References Cited

U.S. PATENT DOCUMENTS

| | | | | |
|---|---|---|---|---|
| 6,086,487 | A | 7/2000 | Morgan et al. | |
| 6,186,002 | B1 | 2/2001 | Lieberman et al. | |
| 6,672,978 | B1 | 1/2004 | Morgan et al. | |
| 6,760,685 | B2 | 7/2004 | Boehm | |
| 6,794,447 | B1 | 9/2004 | Kim et al. | |
| 7,384,352 | B2 | 6/2008 | Ohama et al. | |
| 7,396,301 | B2 | 7/2008 | Ohama et al. | |
| 7,410,430 | B2 | 8/2008 | Isogawa et al. | |
| 7,762,911 | B2 | 7/2010 | Gobush et al. | |
| 7,887,439 | B2 | 2/2011 | Aoyama et al. | |
| 7,908,907 | B1 | 3/2011 | Nelson et al. | |
| 2002/0119828 | A1 | 8/2002 | Toulon et al. | |
| 2002/0152796 | A1 | 10/2002 | Katayama | |
| 2003/0176988 | A1 | 9/2003 | Boehm et al. | |
| 2004/0006442 | A1 | 1/2004 | Boehm | |
| 2005/0085309 | A1 | 4/2005 | McGann et al. | |
| 2006/0030422 | A1 | 2/2006 | Rankin et al. | |
| 2007/0244667 | A1 | 10/2007 | Ligotti, III et al. | |
| 2008/0039236 | A1 | 2/2008 | Isogawa et al. | |
| 2008/0220891 | A1 | 9/2008 | Gobush et al. | |
| 2009/0054175 | A1 | 2/2009 | Isogawa et al. | |
| 2009/0054176 | A1 | 2/2009 | Isogawa et al. | |
| 2009/0082137 | A1 | 3/2009 | Okabe | |
| 2009/0325721 | A1 | 12/2009 | Esayian et al. | |
| 2009/0326688 | A1 | 12/2009 | Thomas et al. | |
| 2010/0210377 | A1 | 8/2010 | Lock | |
| 2010/0323817 | A1* | 12/2010 | Molinari | 473/371 |
| 2011/0009215 | A1 | 1/2011 | Ichikawa et al. | |
| 2011/0098133 | A1 | 4/2011 | Shiga et al. | |
| 2013/0260922 | A1* | 10/2013 | Yontz et al. | 473/409 |

FOREIGN PATENT DOCUMENTS

| | | |
|---|---|---|
| JP | 2006031430 | 2/2006 |
| KR | 10-2007-0106850 | 11/2007 |

* cited by examiner

METHODS FOR PROVIDING A SELECTION OF A RECOMMENDED GOLF BALL

CROSS-REFERENCE TO RELATED APPLICATION

This application claims priority under 35 U.S.C. §119(e) to U.S. Provisional Patent Application No. 61/526,660, entitled "Methods For Selecting Golf Balls," and filed on Aug. 23, 2011, which application is hereby incorporated by reference.

BACKGROUND

The game of golf first centered around striking balls of worked wood around a course. In time, the wooden balls were surpassed in performance by leather-cover, feather-stuffed balls ("featheries"), which were in turn surpassed and replaced by gum-based gutta-percha balls ("gutties"). A century and more ago, balls with thread-wound rubber cores and dimpled covers came to dominate the sport. More modernly, advances in various components of golf ball construction—such as the number of pieces or layers, the materials incorporated therein, and the configuration and number of dimples—have led to improved performance characteristics. Such advances have addressed the constant question: "What would make a golf ball better?"

One challenge involved in making a better golf ball is to improve a golf ball's performance characteristics all the way from the tee to the hole. For example, various components of golf ball construction might be modified to make a ball that is less prone to spinning. The reduced spin may improve a golfer's long game (i.e., shots taken relatively far from a hole) by increasing distances achieved when striking the ball with a driver, such as at the tee. However, a ball that is less prone to spinning may at the same time worsen the golfer's short game (i.e., shots taken relatively near a hole) by hindering a ball's ability to quickly come rest after being struck with a wedge closer to the green. Conversely, modifying various components of golf ball construction to make a ball that is more prone to spinning might improve a golfer's short game by allowing a ball to quickly come to rest when struck with a wedge, but might at the same time hinder the golfer's long game by shortening the trajectory of the ball due to the increased spin on the ball.

There is a need to modify various golf ball construction components in such a way as to improve performance seen not just off the tee, and not just near or on the green, but "across the bag" or at all distances from the hole, i.e., to improve both the long games and the short games of golfers. Accordingly, there is a need to evaluate and provide a selection among various golf balls, or among various golf ball constructions, to assist in the specification and manufacture of golf balls that will improve a golfer's performance across the entire range of golf clubs. In a similar vein, there is a need to evaluate the performance characteristics inherent in a particular golfer's swings in order to assist in providing a selection of a recommended golf ball that may improve the golfer's performance across the entire range of golf clubs.

SUMMARY

In one aspect, the invention includes a method for providing a selection of a recommended golf ball. In one step, the method includes obtaining (a) a first set of measurements for a first golf ball, including at least one ball spin measurement for each of a plurality of golf clubs having different club lofts, and (b) a second set of measurements for a second golf ball, including at least one ball spin measurement for each of the plurality of golf clubs. In another step, the method includes determining (a) a first spin slope based upon the first set of measurements, and (b) a second spin slope based upon the second set of measurements. In another step, the method includes providing a selection of a recommended golf ball between the first golf ball and the second golf ball. The recommended golf ball is the first golf ball if the first spin slope is larger than the second spin slope, and the recommended golf ball is the second golf ball if the first spin slope is not larger than the second spin slope.

In another aspect, the invention includes a method for providing a selection of a recommended golf ball construction. In one step, the method includes obtaining (a) a first set of measurements using a first golf ball having a first ball construction, including at least one ball spin measurement for each of a first golf club having a first club loft and a second golf club having a second club loft, and (b) a second set of measurements using a second golf ball having a second ball construction, including at least one ball spin measurement for each of the first golf club and the second golf club. In another step, the method includes determining (a) a first linear relationship among the first set of measurements, and (b) a second linear relationship among the second set of measurements. In another step, the method includes providing a selection of a recommended golf ball construction between the first ball construction and the second ball construction. The recommended golf ball construction is the first ball construction if a slope of the first linear relationship is larger than a slope of the second linear relationship, and the recommended golf ball construction is the second ball construction if the slope of the first linear relationship is not larger than the slope of the second linear relationship, and wherein the first ball construction is different from the second ball construction.

In another aspect, the invention includes a method for providing a selection of a recommended configuration of a golf ball construction component. In one step, the method includes measuring (a) a first ball spin upon striking a first golf ball with a first golf club having a first club loft, (b) a second ball spin upon striking the first golf ball with a second golf club having a second club loft, (c) a third ball spin upon striking a second golf ball with the first golf club, and (d) a fourth ball spin upon striking the second golf ball with the second golf club. In another step, the method includes determining (a) a first spin slope for the first golf ball, to include the ratio of (1) a difference between the second ball spin and the first ball spin to (2) a difference between the second club loft and the first club loft, and (b) a second spin slope for the second golf ball, to include the ratio of (1) a difference between the fourth ball spin and the third ball spin to (2) the difference between the second club loft and the first club loft. In another step, the method includes providing a selection of a recommended configuration of a golf ball construction component on the basis of at least the first spin slope, the second spin slope, and a spin slope criteria. The configuration of the ball construction component of the second golf ball is different from the configuration of the ball construction component of the first golf ball.

In another aspect, the invention includes a golf ball performance characterization for use in a golf ball fitting system. The golf ball performance characterization comprises a linear relationship among at least a first ball spin measurement, a second ball spin measurement, and a third ball spin measurement. The first ball spin measurement is obtained upon striking a golf ball with a first golf club having a first club loft. The second ball spin measurement being obtained upon striking the golf ball with a second golf club having a second club loft greater than the first club loft. The third ball spin measurement being obtained upon striking the golf ball with a third golf club having a third club loft greater than the second club loft.

In another aspect, the invention includes a method for providing a selection of a recommended golf ball. In one step, the method includes obtaining (a) a first set of ball spin measurements from a player making strikes with a first plurality of striking objects having different lofts, and (b) a second set of ball spin measurements from reference strikes made with a second plurality of striking objects having different lofts. In another step, the method includes determining (a) a first linear relationship among the first set of ball spin measurements, and (b) a second linear relationship among the second set of ball spin measurements. In another step, the method includes providing a selection of a recommended golf ball between a first golf ball and a second golf ball on the basis of at least the first linear relationship, the second linear relationship, and a spin slope criteria. The configuration of a ball construction component of the second golf ball is different from the configuration of the ball construction component of the first golf ball.

In another aspect, the invention includes a method for providing a selection of a recommended golf ball. In one step, the method includes obtaining (a) a first ball spin measurement upon striking a first golf ball with a first golf club having a first club loft, (b) a second ball spin measurement upon striking the first golf ball with a second golf club having a second club loft, (c) a third ball spin measurement associated with striking a second golf ball with a third golf club having a third club loft, and (d) a fourth ball spin measurement associated with striking the second golf ball with a fourth golf club having a fourth club loft. In another step, the method includes determining (a) a first spin slope for the first golf ball, the first spin slope including the ratio of (1) a difference between the second ball spin measurement and the first ball spin measurement to (2) a difference between the second club loft and the first club loft, and (b) a second spin slope for the second golf ball, the second spin slope including the ratio of (1) a difference between the fourth ball spin measurement and the third ball spin measurement to (2) the difference between the fourth club loft and the third club loft. In another step, the method includes providing a selection of a recommended golf ball on the basis of at least the first spin slope, the second spin slope, and a spin slope criteria. The configuration of a ball construction component of the second golf ball is different from the configuration of the ball construction component of the first golf ball.

Other systems, methods, features, and advantages of the invention will be, or will become, apparent to one of ordinary skill in the art upon examination of the following figures and detailed description. It is intended that all such additional systems, methods, features and advantages be included within this description and this summary, be within the scope of the invention, and be protected by the following claims.

BRIEF DESCRIPTION OF THE DRAWINGS

The invention can be better understood with reference to the following drawings and description. The components in the figures are not necessarily to scale; instead, emphasis is placed upon illustrating the principles of the invention. Moreover, in the figures, like reference numerals designate corresponding parts throughout the different views.

DETAILED DESCRIPTION

Methods for providing a selection of a recommended golf ball are described below. Also described are methods for providing a selection of a recommended golf ball construction, as well as methods for providing a selection of a recommended configuration of a golf ball construction component.

Figure 1:
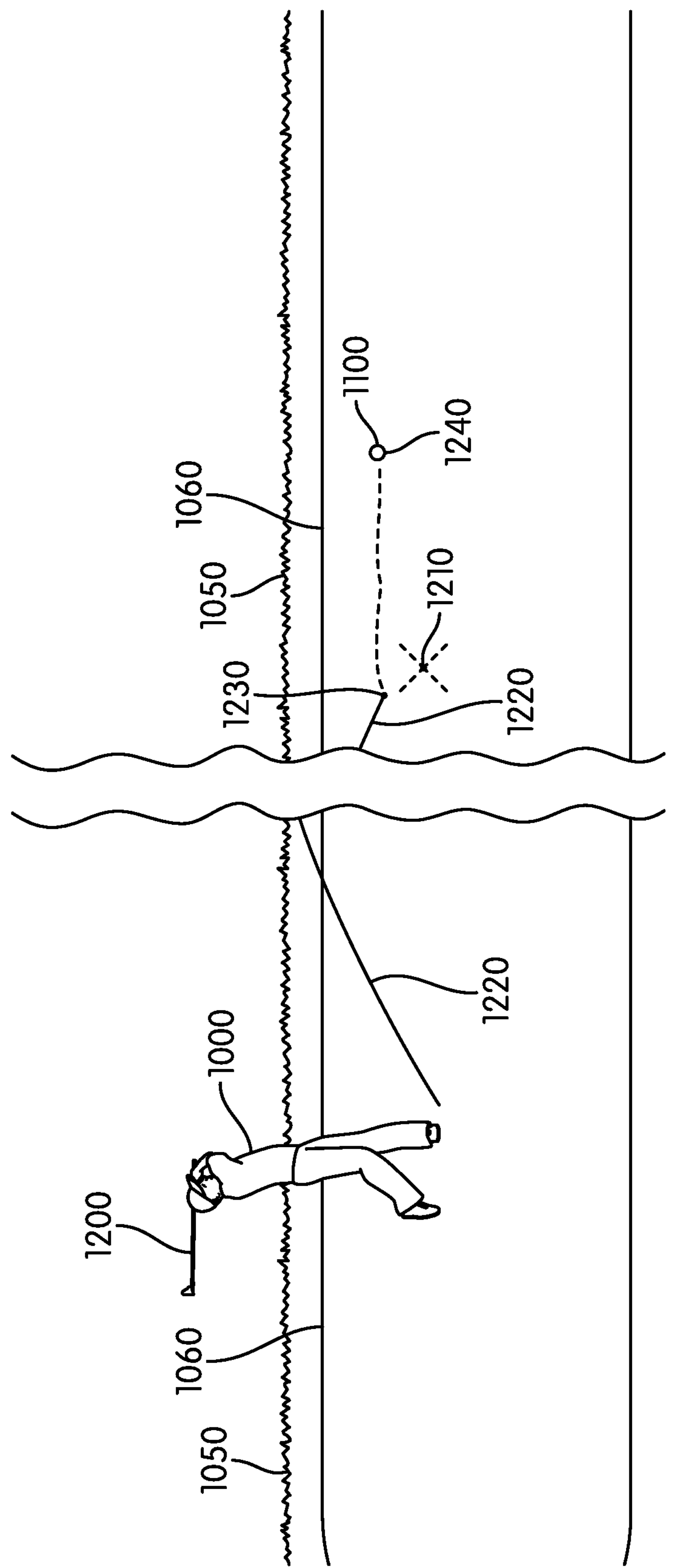
FIG. 1 depicts a golfer using a first embodiment of a golf ball along with a first embodiment of a golf club.
Figure 5:
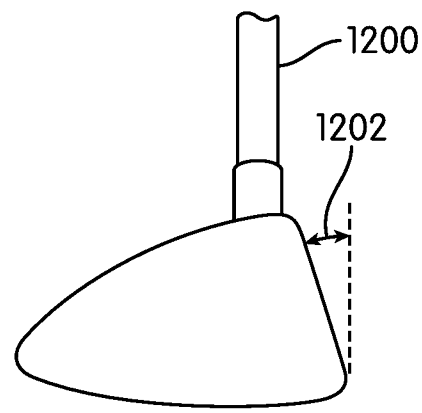
FIG. 5 depicts the first embodiment of the golf club.

FIG. 1 depicts a golfer 1000 playing a game of golf on a fairway 1060 of a golf course 1050. Golfer 1000, still far from the hole, has made a golf shot by swinging at and striking a first golf ball 1100 with a first golf club 1200. Since golfer 1000 is still playing on an early portion of fairway 1060, first golf club 1200 may be a driver, such as a wood, or another club designed primarily to assist golfer 1000 in achieving maximum distance as a result of the swing. As depicted in FIG. 5, first golf club 1200 has a first club loft 1202 representing the angle of the club's face relative to a vertical line (i.e., a line parallel to the club shaft). First club loft 1202 of first golf club 1200 is in the low range of golf club lofts, which helps a golfer maximize the distance achieved on striking a golf ball.

Returning to FIG. 1, in the course of swinging, golfer 1000 has aimed at a first target spot 1210. The strike resulting from the swing has sent first golf ball 1100 along a first trajectory 1220 to hit fairway 1060 at a first contact spot 1230 near first target spot 1210. After hitting first contact spot 1230, first golf ball 1100 may bounce or roll some distance from first contact spot 1230 and come to rest at first stopping spot 1240.

Figure 2:
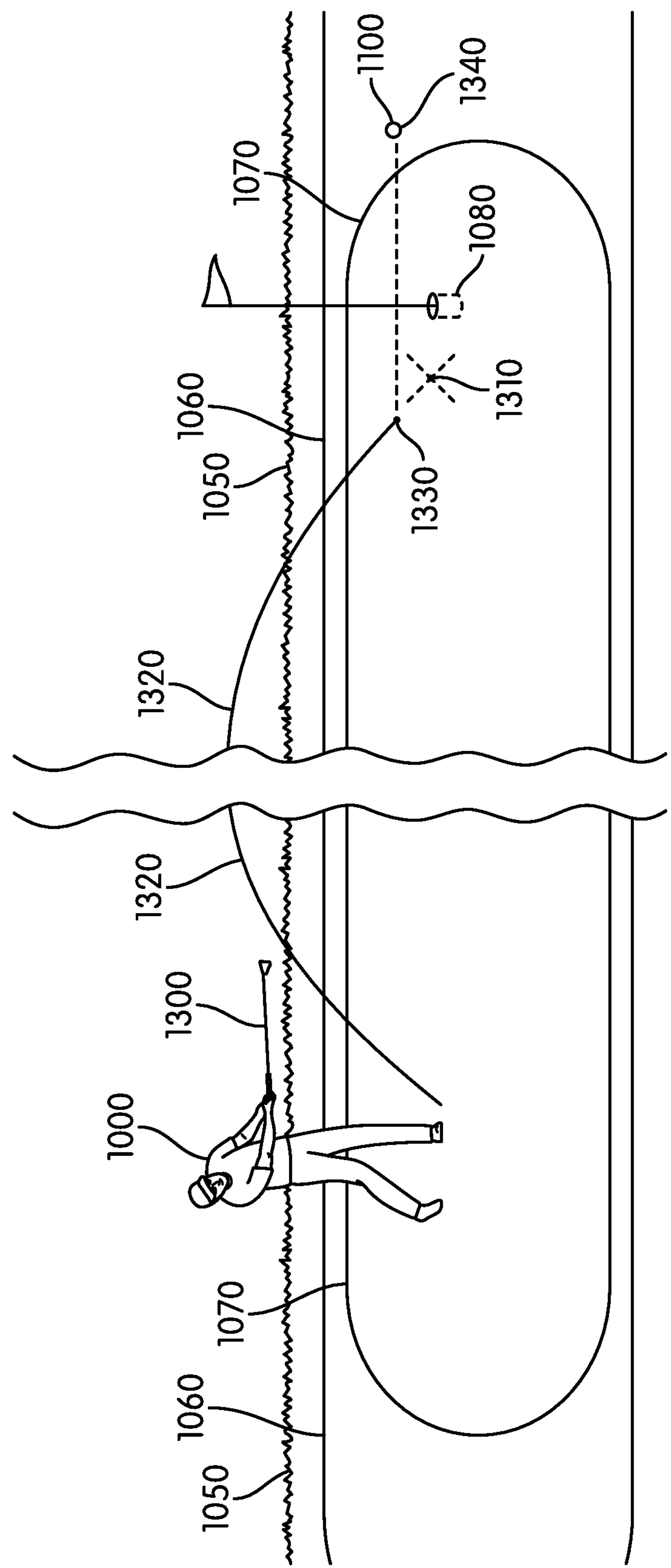
FIG. 2 depicts the golfer using the first embodiment of the golf ball along with a second embodiment of the golf club.
Figure 6:
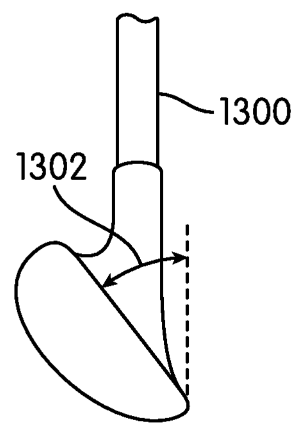
FIG. 6 depicts the second embodiment of the golf club.

Proceeding, FIG. 2 depicts golfer 1000 at a time when play has advanced close to a hole 1080. Golfer 1000, now on a green 1070, has made another golf shot by swinging at and striking first golf ball 1100 with a second golf club 1300. Since golfer 1000 is playing on green 1070 and close to hole 1080, second golf club 1300 may be a wedge, such as a pitching wedge, or another club designed primarily to assist golfer 1000 in achieving a relatively shorter, controlled distance as a result of the swing. As depicted in FIG. 6, second golf club 1300 has a second club loft 1302 representing the angle of the club's face relative to a vertical line (i.e., a line parallel to the club shaft). Second club loft 1302 is in the high range of golf club lofts, which helps a golfer more precisely control the final position of a golf ball achieved upon a strike.

Returning to FIG. 2, in the course of swinging, golfer 1000 has aimed at a second target spot 1310 near hole 1080. The strike resulting from the swing has sent first golf ball 1100 along a second trajectory 1320 to hit green 1070 at a second contact spot 1330 near second target spot 1310. After hitting second contact spot 1330, first golf ball 1100 may bounce or roll some distance from second contact spot 1330 and come to rest at second stopping spot 1340.

Generally speaking, golf shots may be affected by various golf shot parameters. Some golf shot parameters may be swing parameters, and may be influenced by the mechanics or specifics of a golfer's swing. Other golf shot parameters may be launch condition parameters, and may be influenced by both the golfer's swing mechanics and by the construction of a golf ball. Further golf shot parameters may be ball flight parameters, and may be influenced both by the construction of the golf ball and by environmental conditions. Various golf shot parameters may also be influenced by the construction of the golf club used in making the golf shot.

Some swing parameters may include a swing speed, a club path, and an attack angle. The swing speed may be a club head speed. The club path may include a position of the club head, a face angle, or a loft, which may be measured statically at a particular time (such as the moment of impact or contact between ball and club) and with respect to a static or reference position (such as measuring loft and lie angles with respect to a golf club shaft in the vertical plane, for example). The club path may also include a path or direction of the club head, as represented for example by a multi-dimensional vector. The attack angle may be a multi-dimensional angle in a plane defined by a vertical reference direction and an intended or target direction.

Launch condition parameters may include a launch angle, a ball speed or initial velocity, a ball spin, or an initial direction. The ball spin may be either a ball back-spin (i.e., a spin about a horizontal axis) or a ball side-spin (i.e., an angle of backspin relative to a horizontal plane). The initial direction may be an angle relative to an intended target direction, such as an offline angle. Furthermore, an initial angle may be a launch condition parameter combining the launch angle and the offline angle. Launch condition parameters may also include acoustic parameters such as the quality of sound made when a ball is struck.

Ball flight parameters may include parameters related to ball construction, such as dimple count, dimple configuration, and moment of inertia. Ball flight parameters may also include parameters related to environmental conditions, such as wind characteristics (i.e. wind speed and direction), elevation, relative humidity, and weather conditions (i.e. rain, sleet, hail, or snow). Other golf shot parameters may include carry or flight distance, roll distance, and total distance.

Returning to FIGS. 1 and 2, first trajectory 1220 and second trajectory 1320 may be characterized by golf shot parameters such as initial angle, ball back-spin, ball side-spin, and initial velocity. Each of these parameters may be affected by a golfer's choice of golf club. For example, ball back-spin may be relatively low for balls struck with a club like first golf club 1200. In turn, a relatively low ball back-spin may help a golfer maximize the distance achieved on a strike by providing for a relatively straighter trajectory. Alternatively, ball back-spin may be relatively high for balls struck with a club like second golf club 1300. In turn, a relatively high ball back-spin may help a golfer more precisely control the final position of a golf ball achieved upon a strike by counteracting the ball's tendency to bounce or roll away from a contact spot.

At the same time, the construction of a golf ball may affect the golf ball's trajectory upon being hit, such as shape of the trajectory, or the distance over which the trajectory extends. The construction of a golf ball may also affect the manner in which the golf ball bounces or rolls between a contact spot where it hits the ground and a stopping spot where it comes to rest. Accordingly, the construction of first golf ball 1100 may impact first trajectory 1220, the manner in which first golf ball 1100 bounces or rolls between first contact spot 1230 and first stopping spot 1240, or both. Similarly, the construction of first golf ball 1100 may also impact second trajectory 1320, the manner in which first golf ball 1100 bounces or rolls between second contact spot 1330 and second stopping spot 1340, or both.

In general, the construction of a particular golf ball includes a number of components. Pertinent ball construction components may include, for example: the number of pieces or layers within the golf ball; the golf ball's cover material; the hardness of the golf ball's cover material; materials used for one or more core portions, such as an inner core, an outer core, or both, as well as intermediately layers, such as one or more mantle layers, for example; the number of dimples in the golf ball's cover; and the thickness of the golf ball's cover. Other ball construction components may include, for example: the shape, pattern, or other configuration of the dimples in the golf ball's cover; aesthetic considerations such as color or indicia; and other aspects of construction affecting the physical response of the golf ball to external stimulus.

Each piece or layer of the construction used for cover portions of a golf ball as well as for core portions of a golf ball, may have physical characteristics, such as a thickness, and may be formed from any of a variety of materials. Each material used to form a piece or layer of the construction may in turn have physical characteristics such as density, and hardness, for example. Moreover, a physical characteristic of the material within a particular piece or layer of the construction may vary within that piece or layer. The physical characteristic of the material of the piece or layer may not be constant throughout the piece or layer, but may be vary as a function of, for example, a distance at each point within the material from the center of the golf ball. That is, the physical characteristic may be a gradient within the material.

Generally, for any arrangement of layers not specifically mentioned herein, any layer may be made of any material suitable for the purpose. Suitable known materials for use in a golf ball include thermoset materials, such as rubber, styrene butadiene, polybutadiene, isoprene, polyisoprene, certain types of polyurethanes, and trans-isoprene. Known materials also include thermoplastics, such as ionomer resins, polyamides or polyesters, and thermoplastic polyurethane elastomers. Suitable materials also include polyurea compositions, as well as other materials.

For example, a cover layer should be tough and resistant to scuffing while being soft enough for a golf club to impart spin easily to the ball. Thus, thermoplastic polyurethane (TPU) and thermoset polyurethane are suitable for use in cover layers, as are known highly neutralized polymers and other ionomers. Thermoplastic polyurethane that is not otherwise scuff resistant can be treated to harden the surface, such as by a surface treatment or by other treatments before, during, and/or after molding the layer. Suitable ionomers include members of the Surlyn® family of ionomeric polymers produced by E. I. DuPont de Nemours and Company and members of the Iotek® family of products produced by Exxon-Mobil Chemical Corporation. Additionally, other traditional materials for covers may also be used, such as balata.

Each golf ball construction component specifies something about the nature of one or more portions of a golf ball. Accordingly, with respect to FIGS. 1 and 2, when golfer 1000 makes a golf shot by swinging at and striking a golf ball, one or more components of the golf ball's construction may impact the trajectory of the golf ball, or the manner in which the golf ball bounces or rolls between a contact spot where it hits the ground and a stopping spot where it comes to rest.

One or more ball construction components may therefore impact one or more golf shot parameters such as the initial angle, the ball back-spin, the ball side-spin, and the initial velocity. Moreover, a particular configuration of a golf ball construction component may affect the golf ball's trajectory in one way when struck by a club having a low loft angle, and may affect the golf ball's trajectory in another different way when struck by a club having a high loft angle.

Figure 3:
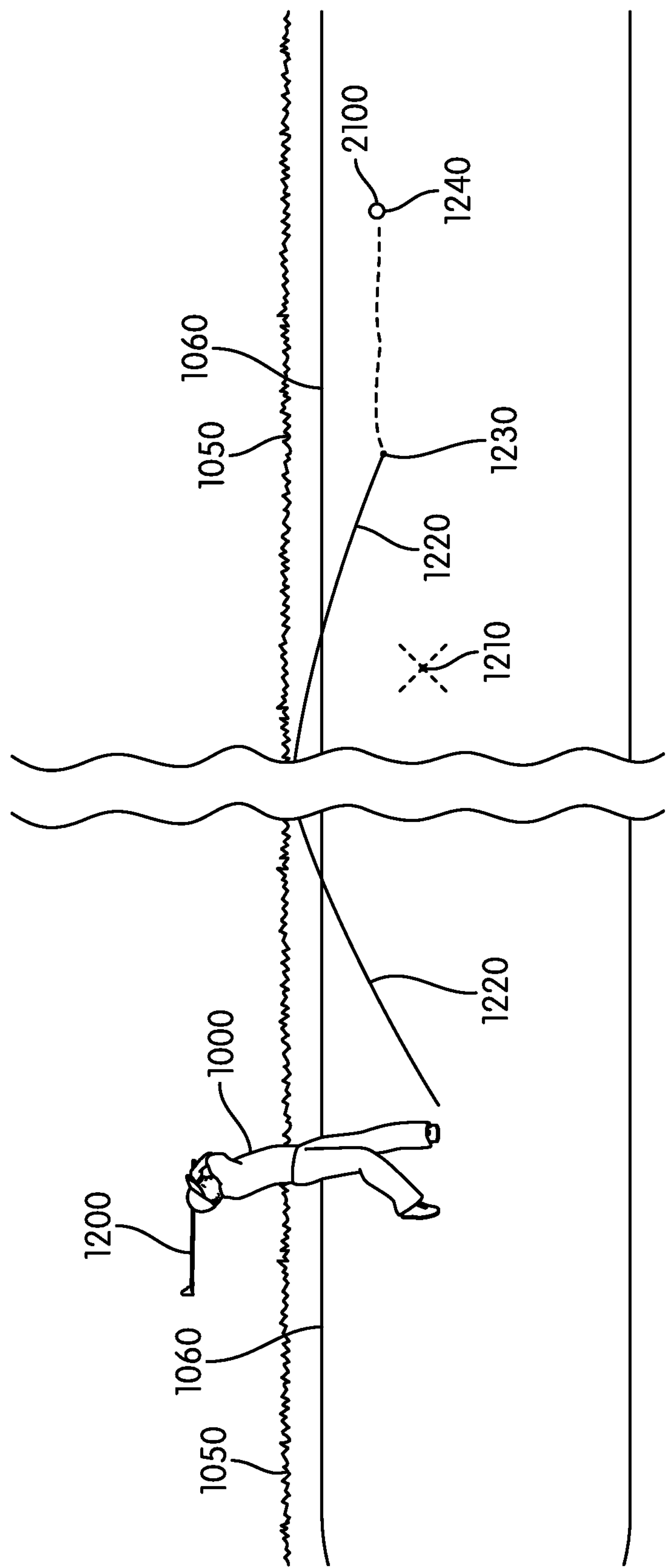
FIG. 3 depicts the golfer using a second embodiment of the golf ball along with the first embodiment of the golf club.

FIG. 3 depicts golfer 1000 playing golf on fairway 1060 of golf course 1050. As with FIG. 1, golfer 1000, being far from the hole, has made a golf shot with first golf club 1200. However, in FIG. 3, golfer 1000 has swung at a second golf ball 2100, which has a construction different from the construction of first golf ball 1100.

More particularly, the configuration of one or more underlying ball construction components in second golf ball 2100 is different from the configuration of the same underlying ball construction components in first golf ball 1100. As a result, second golf ball 2100 may perform differently than first golf ball 1100 would perform given substantially the same swing. Differences in the configurations of the underlying ball construction components between second golf ball 2100 and first golf ball 2200 may impact such golf shot parameters as initial angle, ball back-spin, ball side-spin, and initial velocity.

Golfer 1000 has swung golf club 1200 in substantially the same way in FIG. 3 as in FIG. 1, and has aimed at first target spot 1210. However, due to differences in ball construction components between second golf ball 2100 and first golf ball 1100, first trajectory 1220 for second golf ball 2100 extends over a greater distance. As a result, first contact spot 1230 and first stopping spot 1240 upon using second golf ball 2100 are farther away from golfer 1000 than first contact spot 1230 and first stopping point 1240 upon using first golf ball 1100. Since golfer 1000 has swung first golf club 1200 in substantially the same way in FIG. 3 as in FIG. 1, these differences are due to differences in the underlying ball construction components between second golf ball 2100 and first golf ball 1100, which have impacted golf shot parameters such as initial angle, ball back-spin, ball side-spin, and initial velocity.

For example, differences in one or more ball construction components of second golf ball 2100 may result in the ball back-spin of second golf ball 2100 resulting from a swing of first golf club 1200 being reduced relative to the ball back-spin of first golf ball 1100 resulting from substantially the same swing of first golf club 1200. This reduced ball back-spin of second golf ball 2100 due to the difference in ball construction components may help a golfer maximize the distance achieved on striking second golf ball 2100 with first golf club 1200.

Figure 4:
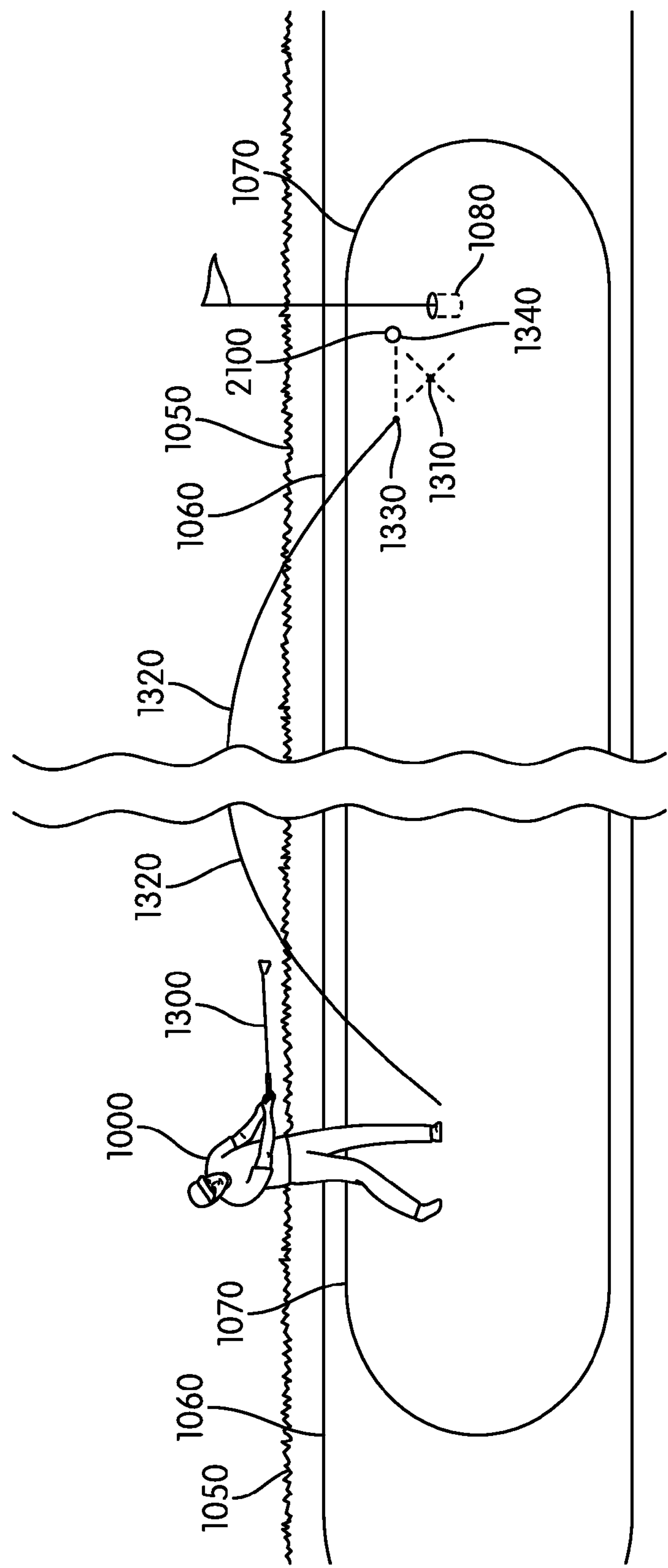
FIG. 4 depicts the golfer using the second embodiment of the golf ball along with the second embodiment of the golf club.

Turning to FIG. 4, golfer 1000 is playing golf on fairway 1060 of golf course 1050, on green 1070. As with FIG. 2, golfer 1000, being on green 1070 and close to hole 1080, has made a golf shot with second golf club 1300. However, in FIG. 4, golfer 1000 has swung at second golf ball 2100.

Golfer 1000 has swung second golf club 1300 in substantially the same was in FIG. 4 as in FIG. 2, and has aimed at second target spot 1310 while swinging, and has achieved substantially the same second trajectory 1320 upon striking second golf ball 2100. However, due to differences in ball construction components between second golf ball 2100 and first golf ball 1100, the manner in which second golf ball 2100 has travelled between second contact spot 1330 and second stopping spot 1340 is different than the manner in which first golf ball 1100 travelled between second contact spot 1330 and second stopping spot 1340. Since golfer 1000 has swung second golf club 1300 in substantially the same way in FIG. 4 as in FIG. 2, these differences are due to differences in the underlying ball construction components between second golf ball 2100 and first golf ball 1100, which have impacted golf shot parameters such as initial angle, ball back-spin, ball side-spin, and initial velocity.

For example, differences in one or more ball construction components of second golf ball 2100 may result in the ball back-spin of second golf ball 2100 resulting from a swing of second golf club 1300 being increased relative to the ball back-spin of first golf ball 1100 resulting from substantially the same swing of second golf club 1300. The increased ball back-spin of second golf ball 2100 due to the difference in ball construction components may help a golfer more precisely control the final position of second golf ball achieved upon striking second golf ball 2100 with second golf club 1300.

Moreover, the different configuration of ball construction components of second golf ball 2100 that may reduce ball back-spin when struck with first golf club 1200 may also advantageously increase ball back-spin when struck with second golf club 1300. In other words, a difference in configuration between the ball construction components of two golf balls may improve results obtained from swings with more than one type of golf club. A change in configuration of any of a number of ball construction components of first golf ball 1100 may accordingly result in improved performance on the golf course with more than one type of golf club.

Figure 7:
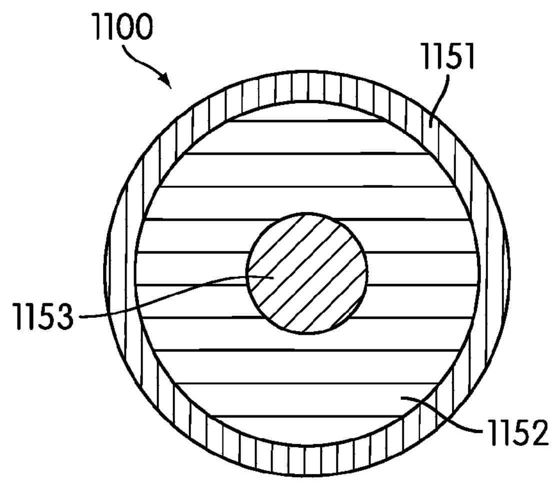
FIGS. 7-9 depict alternate embodiments of the golf ball having different configurations of layers.
Figure 8:
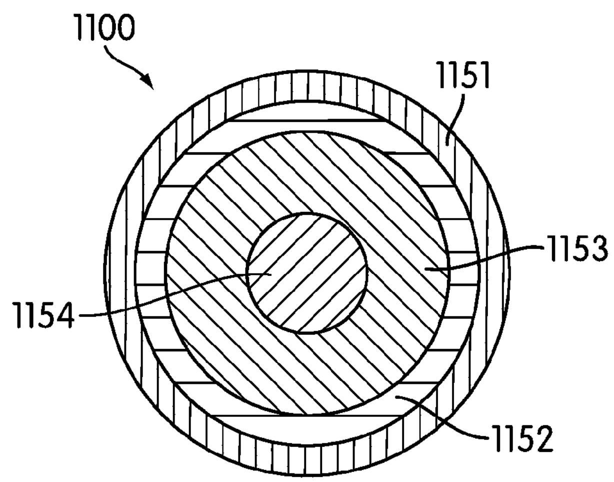
Figure 9:
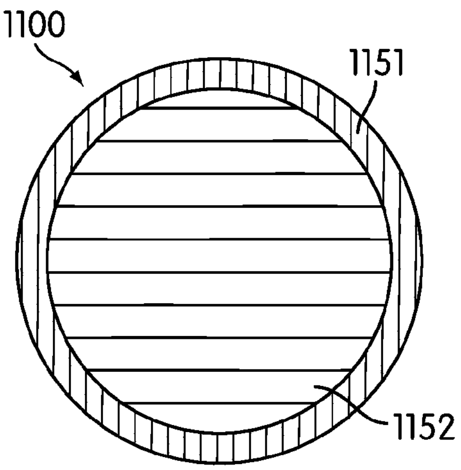

Any of a number of ball construction components of first golf ball 1100 may be modified to alter the performance of first golf ball 1100 when struck by golf clubs 1200 and 1300. As depicted in FIG. 7, first golf ball 1100 may be configured to have a three-piece or three-layer construction including a first layer 1151, a second layer 1152, and a third layer 1153. However, the configuration of first golf ball 1100 may be modified such that golf ball 1100 has more pieces or layers, or fewer pieces or layers. For example, as depicted in FIG. 8, first golf ball 1100 may be configured to have a four-piece or four-layer construction including first layer 1151, second layer 1152, third layer 1153, and a fourth layer 1154. Alternatively, as depicted in FIG. 9, first golf ball 1100 may be configured to have a two-piece or two-layer construction including only first layer 1151 and second layer 1152.

Figure 10:
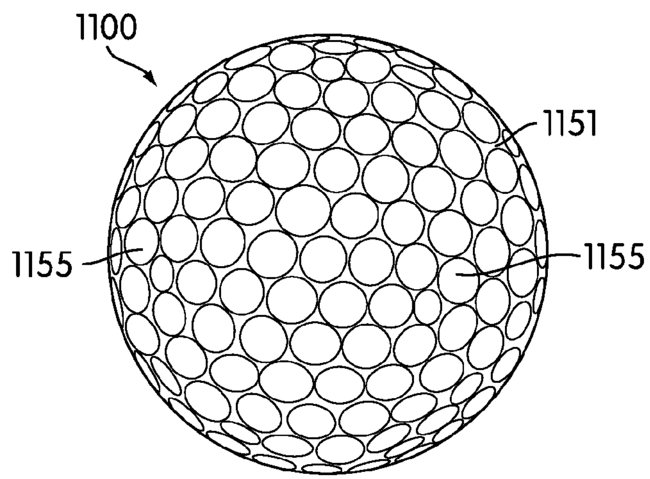
FIGS. 10-12 depict alternate embodiments of the golf ball having different configurations of dimples.
Figure 11:
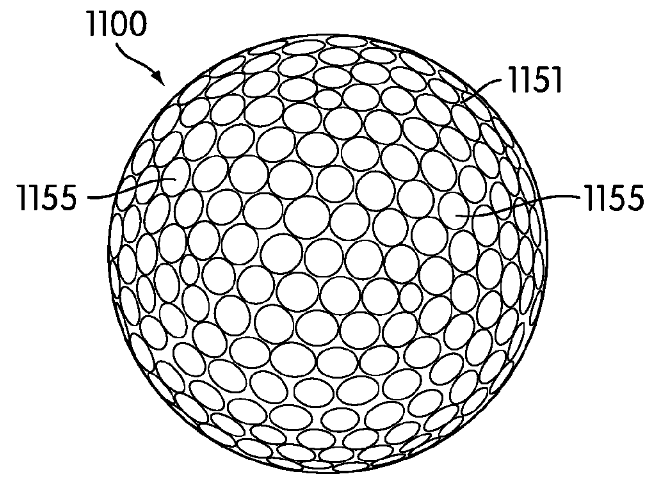
Figure 12:
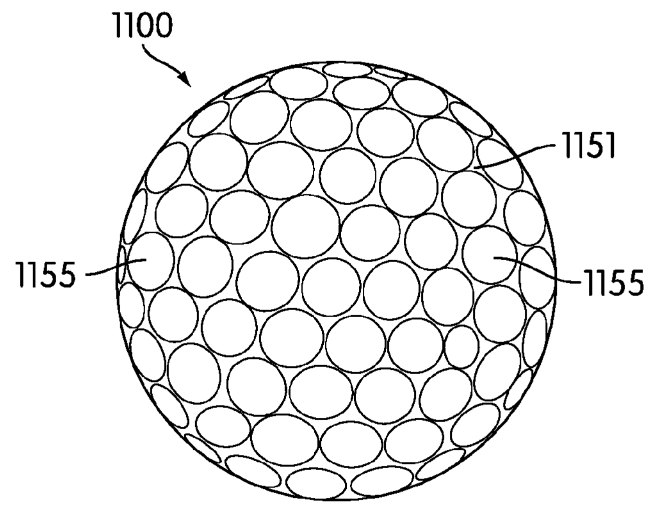

Alternatively, FIG. 10 depicts first golf ball 1100 as having a configuration in which first layer 1151, a cover layer, has a first number of dimples 1155. The configuration of first golf ball 1100 may be modified, though, such that golf ball 1100 has more dimples or fewer dimples. As in the example depicted in FIG. 11, first golf ball 1100 may be configured to have a second number of dimples 1155 greater than the first number of dimples 1155 of FIG. 10. In contrast, as in the example depicted in FIG. 12, first golf ball 1100 may be configured to have a third number of dimples 1155 less than the first number of dimples 1155.

Figure 13:
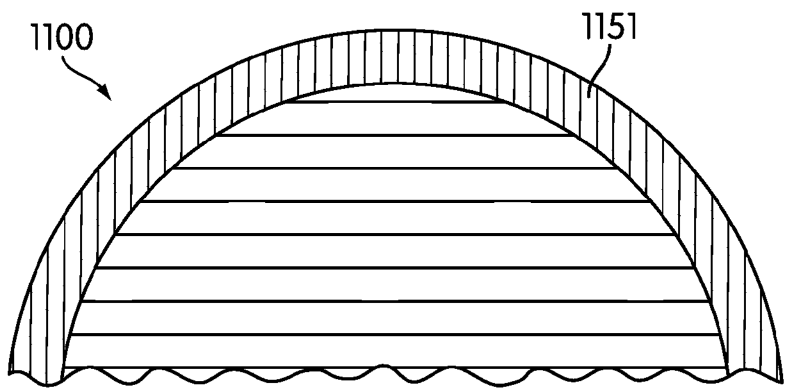
FIGS. 13-15 depict alternate embodiments of the golf ball having different configurations of cover layer thickness.
Figure 14:
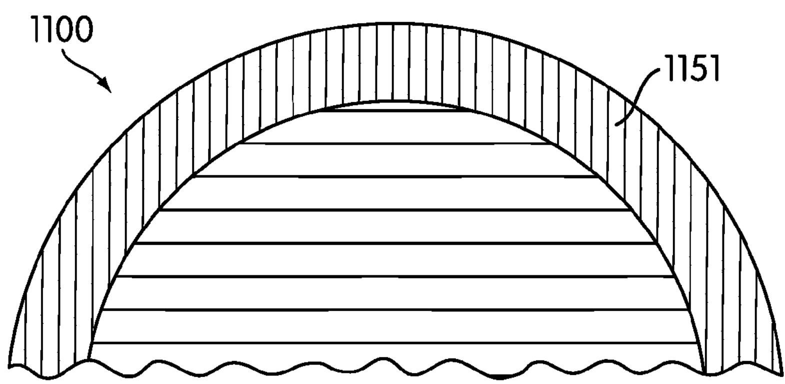
Figure 15:
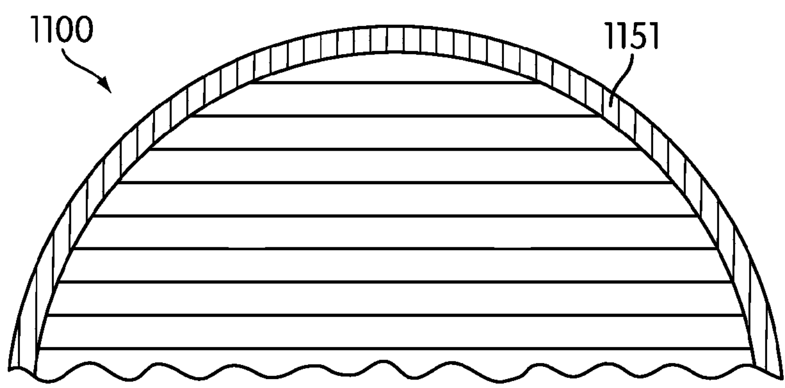

Meanwhile, FIG. 13 depicts golf ball 1100 as having a configuration in which first layer 1151, a cover layer, has a first thickness. In other configurations, first layer 1151 may be modified to have other thicknesses. In one example depicted in FIG. 14, first layer 1151 has been configured to have a second thickness greater than the first thickness. In another example depicted in FIG. 15, first layer 1151 has been configured to have a third thickness less than the first thickness.

Other ball construction components of golf ball 1100 may have alternate configurations as well. For example, the configuration of material or materials incorporated in any of layers 1151-1154 of golf ball 1100 depicted in FIGS. 7-9 may be altered. Moreover, a hardness of a material or materials incorporated in any of layers 1151-1154 of golf ball 1100 may also be altered.

Accordingly, the configuration of various ball construction components of first golf ball 1100 may be modified, as indicated above, to arrive at the ball construction components of second golf ball 1200. Subsequently, the effect on performance due to the modifications of the configuration of first golf ball 1100 may be evaluated. In such evaluations, a first data point 151 may be gathered by striking first golf ball 1100 with first golf club 1200 and a second data point may be gathered by striking first golf ball 1100 with second golf club 1300. Similarly, a third data point 153 may be gathered by striking second golf ball 2100 with first golf club 1200 and a fourth data point may be gathered by striking second golf ball 2100 with second golf club 1300.

As depicted in FIGS. 20-24, each of data points 151-154 may have at least two values and may be graphically represented in a two-value coordinate system, such as x/y coordinate system 100 having an x-axis 110 and a y-axis 120. A first value of data points 151-154 may represent the club loft associated each particular strike, while a second value of data points 151-154 may represent the golf ball back-spin associated with each particular strike. In the context of x/y coordinate system 100, the first values of data points 151-154 may establish x-coordinates of data points 151-154 within x/y coordinate system 100, and the second values of data points 151-154 may establish y-coordinates of data points 151-154 within x/y coordinate system 100.

Therefore, as described above and as depicted in FIGS. 20-24, the first values of data points 151 and 152 would represent, respectively, (a) first club loft 1202 and (b) second club loft 1302, while the second values of data points 151 and 152 would represent, respectively, (a) a ball back-spin value obtained from striking first golf ball 1100 with first golf club 1200, and (b) a ball back-spin value obtained from striking first golf ball 1100 with second golf club 1300. Similarly, the first values of data points 153 and 154 would represent, respectively, (a) first club loft 1202 and (b) second club loft 1302, while the second values of data points 153 and 154 would represent, respectively, (a) a ball back-spin value obtained from striking second golf ball 2100 with first golf club 1200, and (b) a ball back-spin value obtained from striking second golf ball 2100 with second golf club 1300.

Moreover, a first line may relate data points 151 and 152 to each other, and a second line may relate data points 153 and 154 to each other. Each of the first line and the second line may have a "spin slope" that is the ratio of a difference between y-values of a set of two points along the line to a difference between x-values of the same set of two points (i.e., a ratio of "rise" to "run" along the line). For example, a first spin slope 201 of the line relating first data point 151 to second data point may be the ratio of (1) the difference between the y-value of second data point 152 and the y-value of first data point 151 to (2) the difference between the x-value of second data point 152 and the x-value of first data point 151. First spin slope 201 may accordingly be a spin slope associated with first golf ball 1100. Similarly, a second spin slope 202 may be a spin slope associated with second golf ball 2100.

Figure 16:
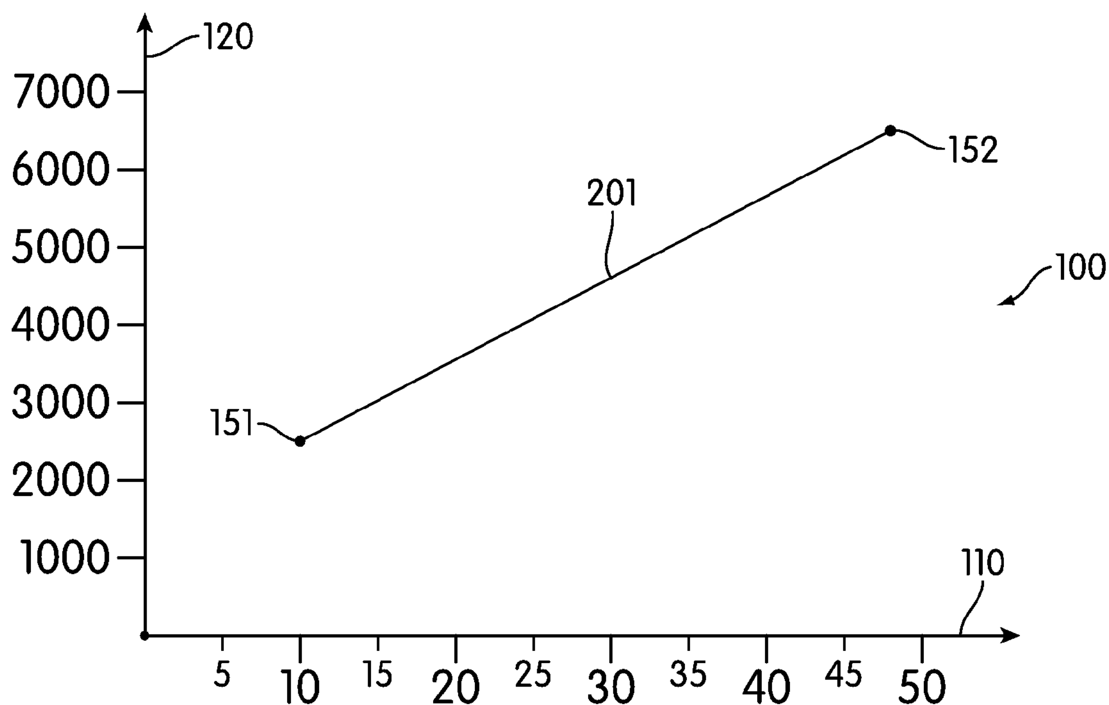
FIG. 16 depicts a set of data points corresponding with the first embodiment of the golf ball, and a slope therebetween, in an x/y coordinate system.

The x-values and y-values associated with each data point may be values as objectively measured, or they may be reduced or simplified representations of objectively-measured values. For example, as depicted in FIG. 16, the x-values are club lofts, measured in degrees, while the y-values are ball back-spins, measured in RPM (revolutions per minute).

Figure 17:
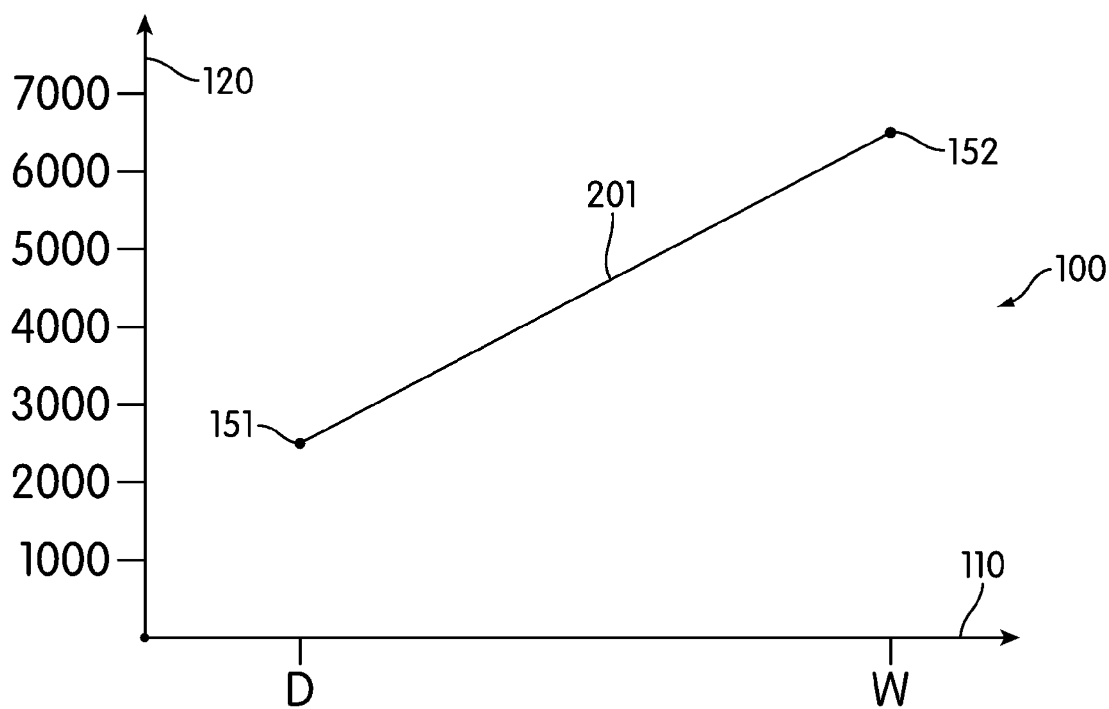
FIGS. 17-19 depict alternate embodiments of the x/y coordinate system.

In contrast, as depicted in FIG. 17, the x-values are reduced or simplified representations of objectively-measured values. In particular, the x-axis has been normalized such that data point 151 obtained by striking a golf ball with first golf club 1100 has an x-value represented as "D," while data point 152 obtained by striking a golf ball with second golf club 1200 has an x-value represented as "W." In such reduced or simplified depictions, the difference between the x-values of data points 151 and 152 may be arbitrarily set to "1," and the spin slope 201 of the line relating data points 151 and 152 reduces to a difference between the y-values (i.e., the ball back-spin) of data points 151 and 152. That is, spin slope 201 reduces to a normalized difference between the ball back-spin values of data point 151 and 152.

Figure 18:
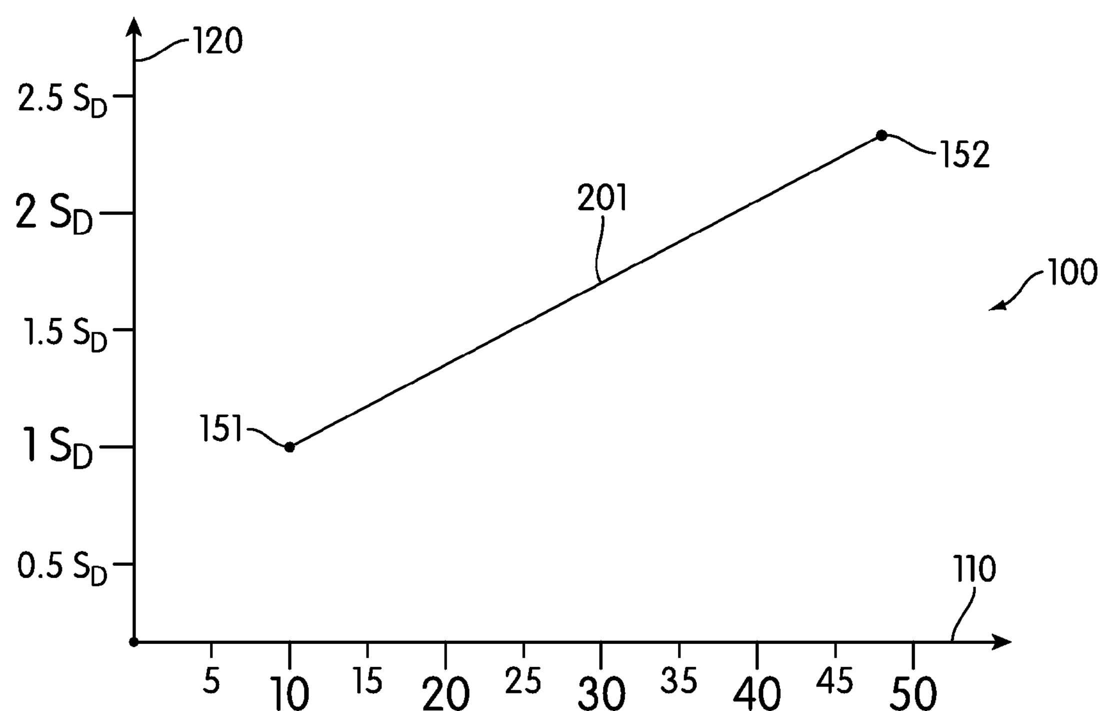

Alternatively, as depicted in FIG. 18, the x-values of data points 151 and 152 are objectively-measured values, while the y-values of data points 151 and 152 are normalized relative to the lowest y-value (i.e., the y-value of data point 151) and are represented along y-axis 120 as multiples of a number labeled $S_D$. In turn, $S_D$ may be the ball back-spin associated with first golf club 1200, which may be a driver. In such reduced or simplified depictions, the y-value of data point 151 is reduced to 1 $S_D$, while the y-value of data point 152 is reduced to approximately 2.25 $S_D$. That is, spin slope 201 becomes the ratio of a difference in the normalized multiple of $S_D$ units between data points 151 and 152 to the difference between the x-values (i.e., club lofts) of data points 151 and 152.

Figure 19:
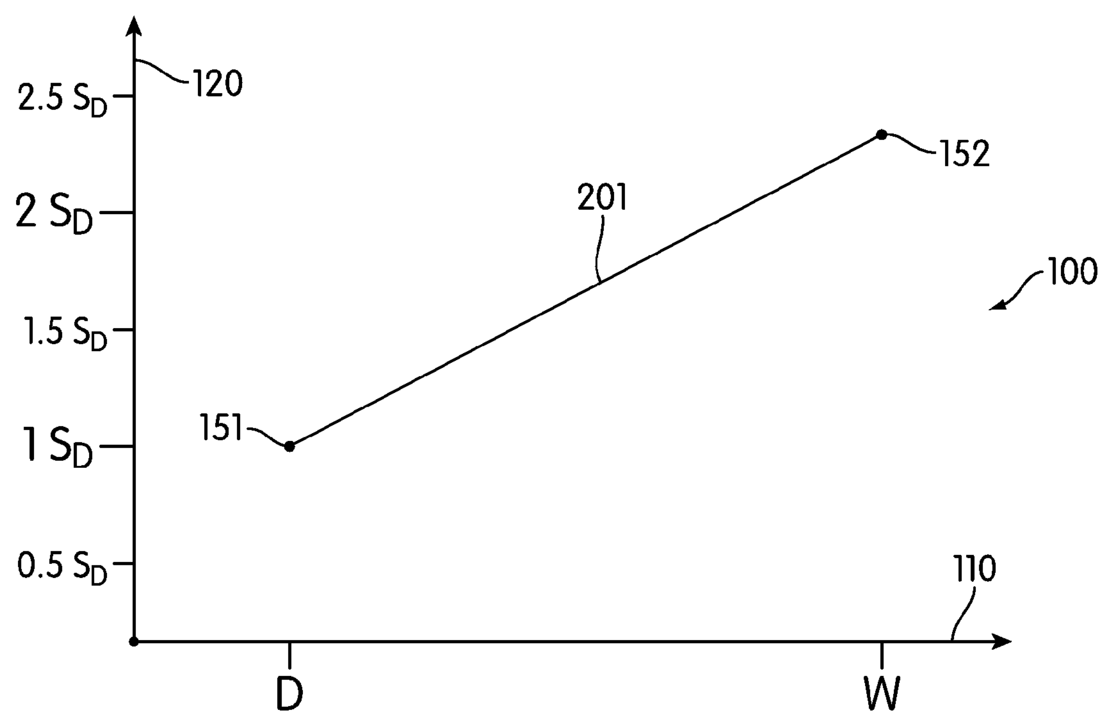

As a further alternative, both the x-values and the y-values may be reduced or simplified. For example, as depicted in FIG. 19, the reduction or simplification of x-values of FIG. 17 is combined with the reduction or simplification of y-values of FIG. 18, such that spin slope 201 reduces to of a normalized multiple of $S_D$ units between data points 151 and 152.

The differing configurations of ball construction components between first golf ball 1100 and second golf ball 1300 may result in differing responses, such as differing ball back-spin measurements, upon strikes made with first golf club 1200, second golf club 1300, or both. In various configurations of ball construction components, the ball back-spin of second golf ball 2100 might be greater than or less than the ball back-spin of first golf ball 1100 when struck by either first golf club 1200 or second golf club 1300.

Figure 20:
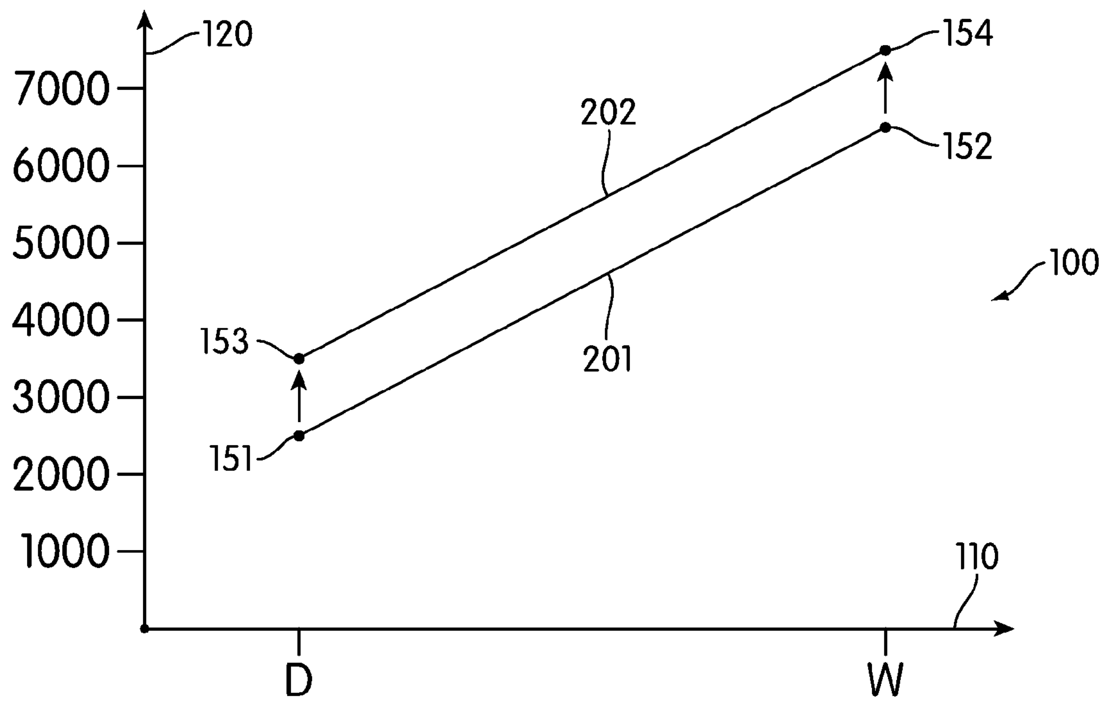
FIG. 20 depicts sets of data points associated with the first embodiment of the golf ball and the second embodiment of the golf ball, and the slopes therebetween.
Figure 21:
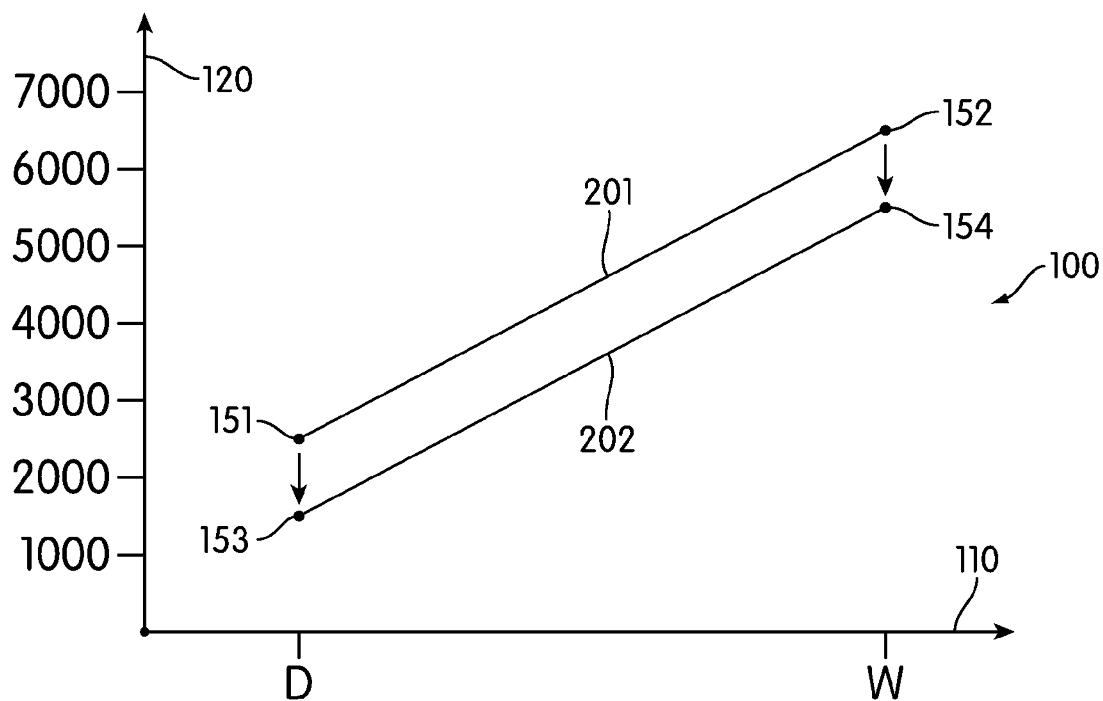
FIGS. 21-24 depict sets of data points associated with alternate embodiments of the golf ball.

For example, as depicted in FIG. 20, ball back-spin values for data points 153 and 154 corresponding with second golf ball 1200 are greater than ball back-spin values for data points 151 and 152 corresponding with first golf ball 1100. That is, second golf ball 2100 is measured as having a greater ball back-spin than first golf ball 1200 when struck either with first golf club 1200 or with second golf club 1300. In contrast, as depicted in FIG. 21, second golf ball 2100 is measured as having less ball back-spin than first golf ball 1100 when struck either with first golf club 1200 or with second golf club 1300. Accordingly, as depicted in FIGS. 20 and 21, the second spin slope 202 and the first spin slope 201 are substantially similar.

Figure 22:
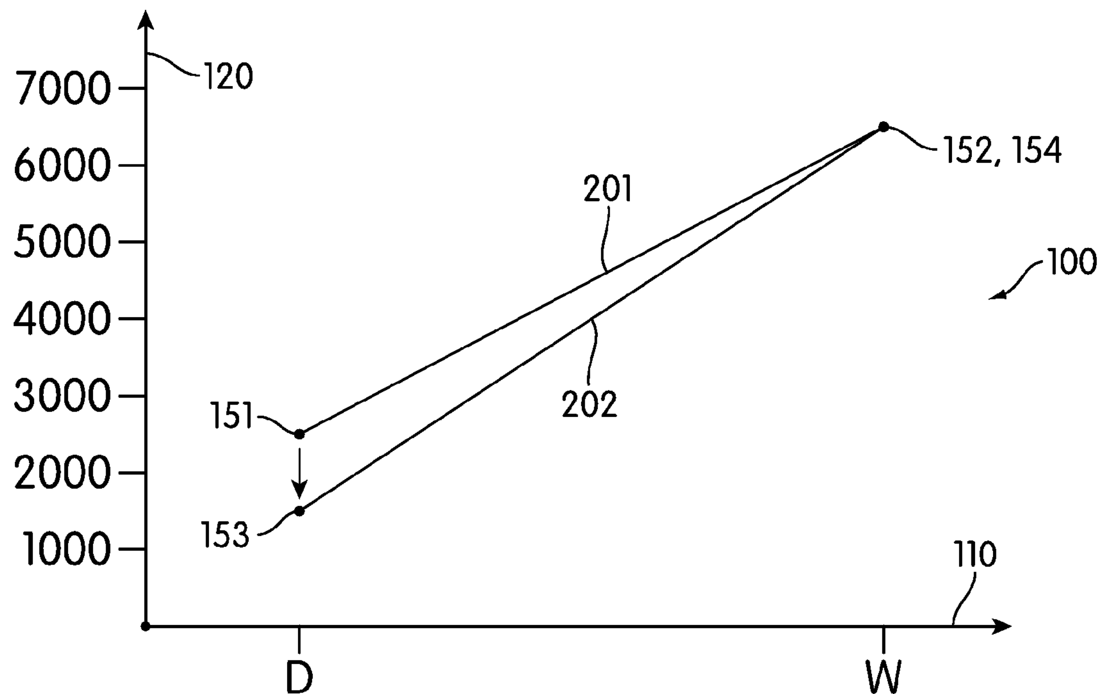

In other configurations, the ball back-spin of second golf ball 2100 might differ from the ball back-spin of first golf ball 1100 when struck by either first golf club 1200 or second golf club 1300, but not both. For example, as depicted in FIG. 22, a ball back-spin value for data point 153 is less than a ball back-spin value for data point 151, while ball back-spin values for data points 152 and 154 are substantially similar.

Figure 23:
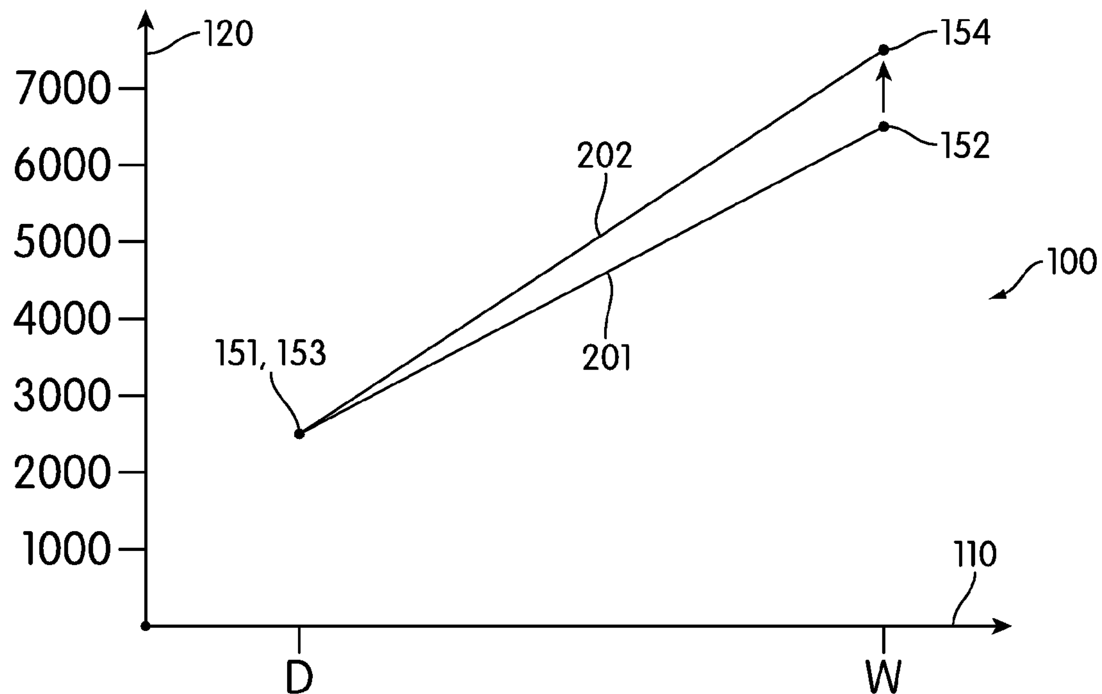

Alternatively, as depicted in FIG. 23, a ball back-spin value for data point 154 is greater than a ball back-spin value for data point 152, while ball back-spin values for data points 151 and 153 are substantially similar. Accordingly, as depicted in FIGS. 22 and 23, the second spin slope 202 is greater than first spin slope 201. Ball configurations producing ball back-spin values that change for either first golf club 1200 or second golf club 1300, but not both (i.e., that do not change ball back-spin values across the bag), may be useful for golfers who need more spin in some areas of their game than in others.

Figure 24:
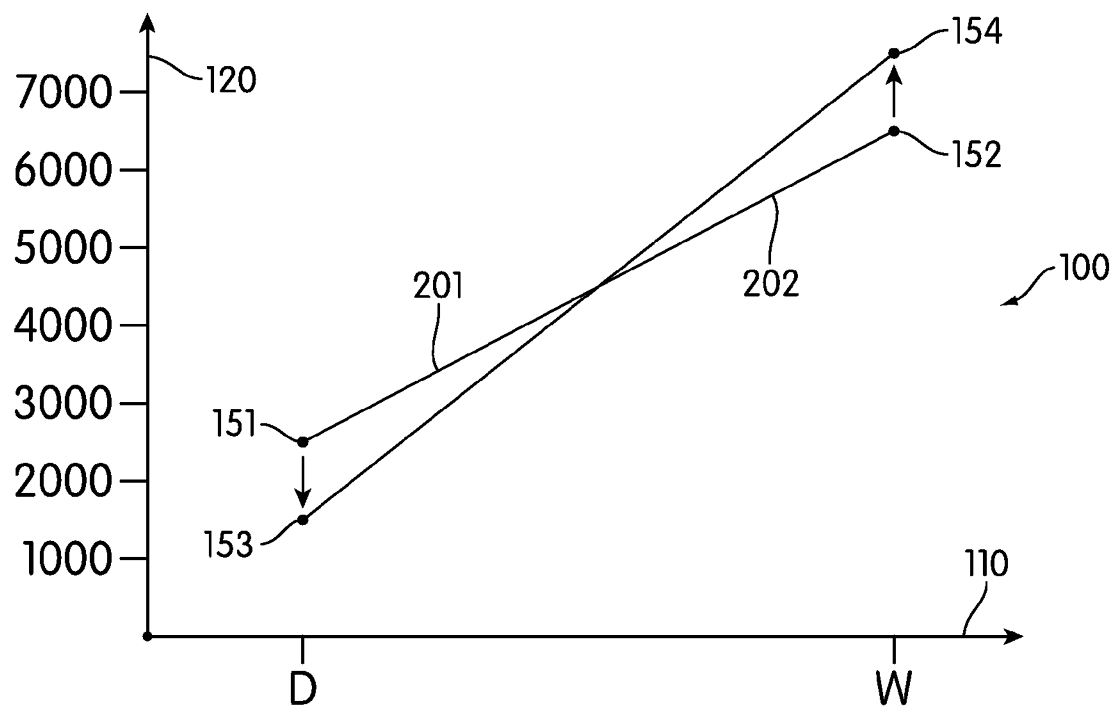

In still further configurations, the ball back-spin of second golf ball 2100 might be less than the ball back-spin of first golf ball 1100 when struck by first golf club 1200, but might be greater than the ball back-spin of first golf ball 1100 when struck by second golf club 1300. For example, as depicted in FIG. 24, a ball back-spin value for data point 153 is less than a ball back-spin value for data point 151, and a ball back-spin value for data point 154 is greater than a ball back-spin value for data point 152. Accordingly, the second spin slope 202 is greater that the first spin slope 201.

Figure 25:
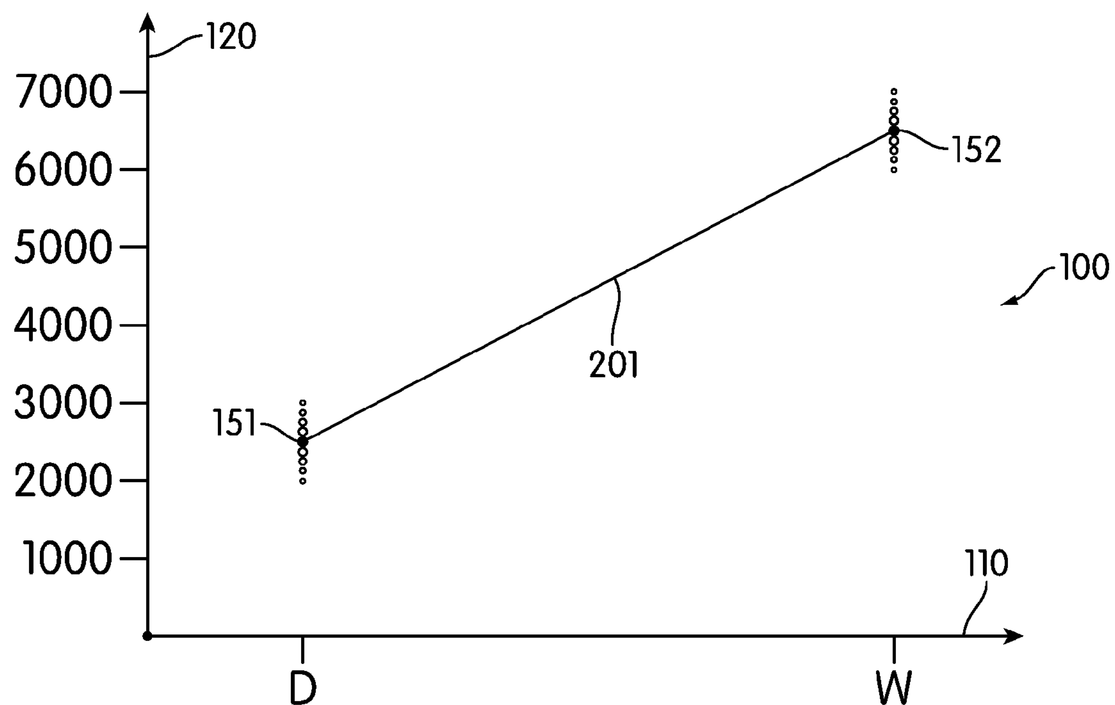
FIG. 25 depicts a set of data points associated with another alternate embodiment of the golf ball.

Data points such as those described above may include composite measurements. For example, y-values (i.e., ball back-spin) values may be statistically extracted from a desired set of measurements, such as repeated measurements of ball back-spin taken under substantially similar conditions. Values that may be statistically extracted from such sets of measurements may include average or mean values, including arithmetic means or geometric means, median values, or standard deviations. As depicted in FIG. 25, for example, data points 151 and 152 both include composite measurements representing the average value of set of measurements having a substantially normal distribution.

Figure 26:
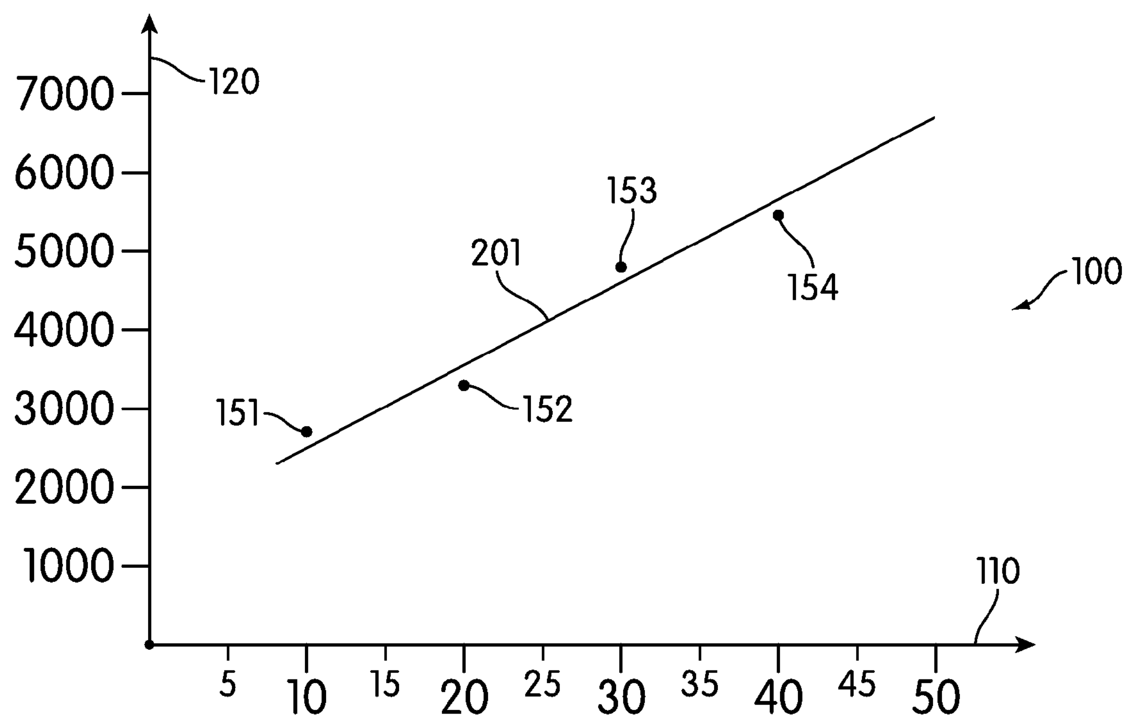
FIGS. 26-27 depict further alternate sets of data points associated with further alternate embodiments of the golf ball.

Additionally, while spin slope may be determined from data points associated with two distinct values of club loft, as discussed above, linear relationships between data points associated with more than two distinct values of club loft. Once such a linear relationship has been determined, a slope may be determined on the basis of that linear relationship. For example, as depicted in FIG. 26, four data points 151, 152, 153, and 153 corresponding with ball back-spin measurements have been obtained using four golf clubs having club lofts of 10 degrees, 20 degrees, 30 degrees, and 40 degrees, respectively. Using standard statistical methods, such as linear regression methods, a linear relationship (i.e., a line equation) that best fits data points 151-154 may be determined. Once such a linear relationship has been determined, slope 201 may be the slope of the corresponding line equation.

Figure 27:
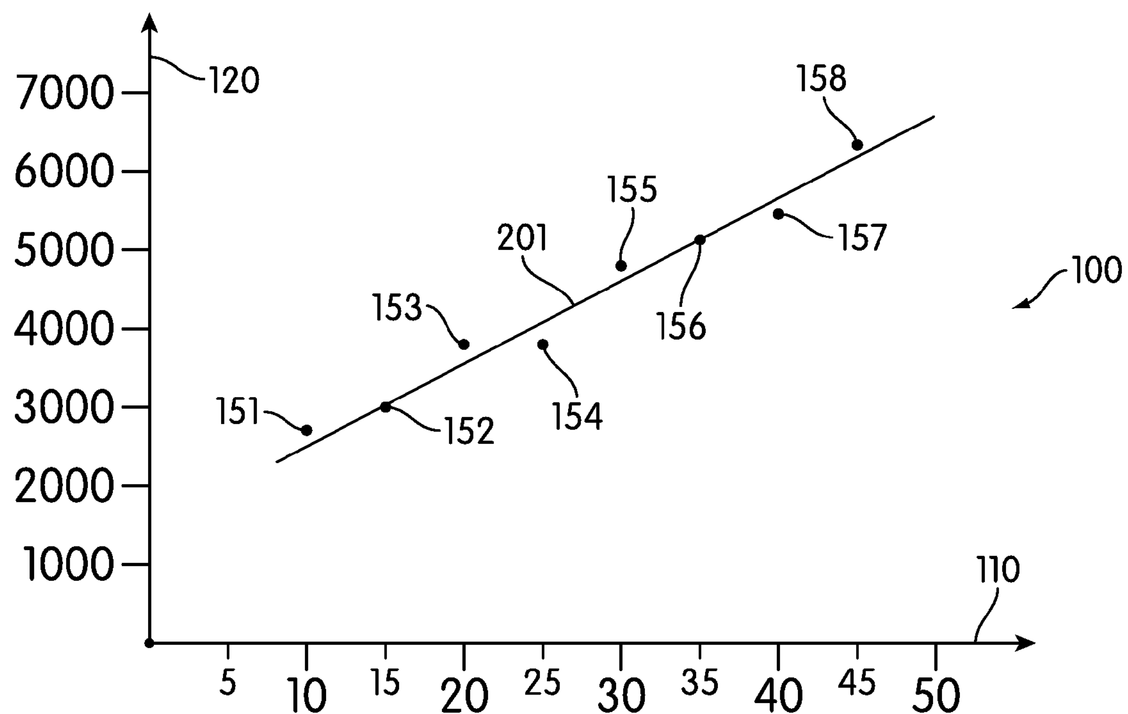

Any number of such data points may be included in a best-fit line determination. As depicted in FIG. 27, eight data points 151-158 corresponding with ball back-spin measurements have been obtained using eight golf clubs having club lofts from 10 degrees through 45 degrees, in 5-degree increments. A linear relationship that best fits data points 151-158 may be determined, and once such a linear relationship has been determined, slope 201 may be the slope of the corresponding line equation.

In addition to characterizing golf ball performance on the basis of a linear spin slope, golf ball performance may also be characterized on the basis of spin as a general function of club loft. In such alternative characterizations, spin as a function of club loft may be represented as a non-straight-line function in x/y coordinate system 100. Some non-straight-line spin functions may be considered to have a plurality of ranges of club loft, and within each range of club loft the measured ball spin may have separate linear relationships, such as separate best-fit lines having different corresponding line equations.

Club lofts may also change among different sets of golf clubs. For example, a particular numerically-designated golf club (i.e., a 9-iron) in one set of golf clubs may have a different club loft than a golf club of the same numerical designation (i.e., another 9-iron) in a different set of golf clubs. Accordingly, spin slope determinations may made separately made using two different sets of golf clubs corresponding with two different sets of club lofts, and thereafter compared with each other, despite the difference in club loft among the various golf clubs of the two different sets.

Determinations of spin slope as described above may be used in methods for providing a selection of a recommended golf ball. In such methods, first spin slope 201 may be calculated with respect to first golf ball 1100, second spin slope 202 may be calculated with respect to second golf ball 1200, and the recommended golf ball may be either first golf ball 1100 or second golf ball 1200 based upon first spin slope 201 and second spin slope 202. For example, the recommended golf ball may be first golf ball 1100 if first spin slope 201 is greater than second spin slope 202, while the recommended golf ball may be second golf ball 1200 if second spin slope 202 is greater than first spin slope 201.

In calculating various spin slopes, with reference to FIGS. 20-24, data points 151-154 may be obtained by directly measuring ball back-spin upon striking golf balls 1100 and 1200 with various golf clubs. However, data points 151-154 may be otherwise obtained. For example, data points 151-154 may be measured beforehand, and may serve as numerical inputs to methods for providing a selection of a recommended golf ball.

As discussed above, data points 151-154 may be obtained under substantially similar conditions. For example, both the set of data points 151 and 152 as well as the set of data points 153 and 154 may be collected through mechanical, machine-based, or otherwise automated striking of golf balls. In alternate methods, one set of data points may be obtained from a player striking a reference golf ball, and the other set may be a reference set of measurements corresponding with the reference golf ball. The reference golf ball may be a preselected golf ball used in collecting data points, or it may be a golf ball of predetermined construction, such as a USGA calibration or control ball.

For example, data points 151 and 152 may be a reference set of measurements corresponding with a reference golf ball, while data points 153 and 154 may be obtained from a player striking the reference golf ball, for purposes of custom-fitting a particular player to a particular golf ball on the basis of spin slope. In such methods, when first spin slope 201 is greater than second spin slope 202, the recommended golf ball may be a first golf ball, whereas when second spin slope 202 is greater than first spin slope 201, the recommended golf ball may be a second golf ball different from the first golf ball. The selection of the recommended golf ball may in turn reflect the better suitability of the first golf ball or the second golf ball for the player, on the basis of the relationship between the reference spin slope and the spin slope determined from measurements of the player's strikes.

Alternatively, some players may prefer golf balls having lesser spin slopes. Such preferences may relate to factors such as a player's experience level and a player's preferred ball performance characteristics. In custom-fitting such players to particular golf balls on the basis of spin slope, when first spin slope 201 is less than second spin slope 202, the recommended golf ball may be the first golf ball, whereas when second spin slope 202 is less than first spin slope 201, the recommended golf ball may be the second golf ball.

In addition to being used in methods for providing a selection of a recommended golf ball, determinations of spin slope may be used in methods for providing a selection of a recommended golf ball construction between a plurality of golf ball constructions. For example, a first golf ball may have a first ball construction and a second golf ball may have a second, different ball construction. A set of spin measurements may be obtained for each golf ball based upon which a spin slope may be determined for each golf ball. Then, if the spin slope corresponding with the first golf ball is greater than the spin slope corresponding with the second golf ball, the recommended golf ball construction may be the first ball construction; or, if the spin slope corresponding with the second golf ball is greater than the spin slope corresponding with the first golf ball, the recommended golf ball construction may be the second ball construction.

Moreover, determinations of spin slope may be used in methods for providing a selection of a recommended configuration of one or more particular ball construction components. For example, a first golf ball may have a first configuration of a particular ball construction component, and a second golf ball may have a second, different configuration of the same ball construction component. A set of spin measurements may be obtained for each golf ball based upon which a spin slope may be determined for each golf ball. Then, if the spin slope corresponding with the first golf ball is greater than the spin slope corresponding with the second golf ball, the recommended configuration of the particular ball construction component may be the first configuration of the ball construction component; or, if the spin slope corresponding with the second golf ball is greater than the spin slope corresponding with the first golf ball, the recommended configuration of the particular ball construction component may be the second configuration of the ball construction component.

In some methods, alternate spin slope criteria may be used in for providing a selection between a plurality of golf balls, golf ball constructions, or configurations of ball construction components. As discussed above, a recommended golf ball may be a first golf ball when the first golf ball (or a golf ball construction of the first golf ball, or a configuration of a ball construction component corresponding with the first golf ball) results in a greater or larger spin slope than the spin slope of a second golf ball. In contrast, under an alternate spin slope criteria, a recommended golf ball may be a first golf ball when the first golf ball (or a golf ball construction of the first golf ball, or a configuration of a ball construction component corresponding with the first golf ball) results in a lesser or smaller spin slope than the spin slope of a second golf ball. In general, slope is a measurement of the amount or degree of "steepness" of a line relative to the horizontal axis. Accordingly, when comparing the relative measures of spin slope described herein, the greater or larger slope is the slope that exhibits a greater or larger degree of steepness relative to the horizontal. Similarly, the lesser or smaller slope is the slope that exhibits a lesser or smaller degree of steepness relative to the horizontal.

Additionally, methods of providing a selection of a recommended golf ball construction may also include a step of manufacturing a golf ball in accordance with the recommended golf ball construction. Similarly, methods of providing a selection of a recommended configuration of a golf ball construction component may also include a step of manufacturing a golf ball in accordance with the recommended configuration of the golf ball construction component.

The methods discussed above may also be used to obtain measurements of golf shot parameters other than ball spin, and may be used to determine slopes with respect to those other golf shot parameters. For example, some methods may obtain measurements related to parameters such as flight distance, carry distance, or total distance. Such methods may then determine a distance slope with respect to that parameter by (a) obtaining sets of distance measurements, each set containing measurements corresponding with a plurality of golf clubs, then (b) determining a distance slope for each set of distance measurements. The distance slopes would in turn be the ratio of a difference between distance measurements to a difference between club loft among two or more points within each set.

In addition, the methods discussed above may be used to evaluate performance characteristics of various golf clubs, such as spin slope characteristics for various golf clubs. By way of example, the methods described above may be used to obtain measurements of golf shot parameters, such as ball back-spin, for a plurality of golf clubs to be compared with each other, using a reference golf ball. The ball back-spin measurements obtained for each of the plurality of golf clubs may then be used to determine separate spin slopes for each club and provide a selection of a recommended golf club between the plurality of golf clubs upon based upon a comparison of the spin slopes.

The use of calibration balls may be incorporated into the methods discussed above. A calibration ball, or control ball, may be a ball satisfying specifications established by the USGA (United States Golf Association) in a particular year. Calibration balls may be used to compare the characteristics of a plurality of golf clubs, or of a plurality of golf swing sources, including golf swings taken by golfers and golf swings taken by machines. The characteristics being compared may therefore include various swing parameters, launch condition parameters, and other golf shot parameters.

For example, a calibration ball may be used in the course of obtaining a set of ball back-spin measurements for a plurality of golf clubs under controlled testing conditions, for example tests performed under laboratory conditions or using an indoor test range. The ball back-spin measurements may be obtained with care being taken to ensure that various testing conditions are substantially the same, and are within standard engineering and testing tolerances. On the basis of the ball back-spin measurements, a benchmark linear relationship among the measurements may be determined for the calibration ball.

Ball back-spin measurements may then be similarly taken for one or more other balls under substantially the same controlled testing conditions, and benchmark linear relationships among the measurements for each of those balls may be determined. The slopes of the benchmark linear relationships for the other balls may then be expressed as being normalized with respect to the slope of the benchmark linear relationship for the calibration ball. For example, if the linear relationships are straight lines, the slope for each of the other balls may be a number normalized with respect to the slope for the calibration ball. The slope for the calibration ball may thus serve as a baseline slope against which the spin slopes of other balls may be compared.

For example, in FIG. 20, data points 151 and 152 may correspond with a calibration ball, and data points 153 and 154 may correspond with another ball under measurement. Accordingly, first spin slope 201 may be a benchmark linear relationship for the calibration ball, and second spin slope 202 may be a linear relationship for the other ball. First spin slope 201 may serve as a baseline slope having a value of 1. Second spin slope 202, which is substantially similar to first spin slope 201, may have substantially the same value as the baseline slope, i.e., a value of 1. Similarly, in FIG. 21, first spin slope 201 may serve as a baseline slope having a value of 1, and second spin slope 202 may also have substantially the same value.

In contrast, as depicted respectively in FIGS. 22, 23, and 24, a ball back-spin value for data point 151 may be greater than a ball back-spin value for data point 153 (when struck by, for example, a driver), or a ball back-spin value for data point 152 may be less than a ball back-spin value for data point 154 (when struck by a wedge, for example), or both. Accordingly, first spin slope 201 may serve as a baseline slope having a value of 1, and second spin slope 202 may have a value greater than 1, as normalized with respect to first spin slope 201.

Having obtained a baseline slope for the benchmark linear relationship for the calibration ball, as well as benchmark linear relationships for other balls, another set of ball back-spin measurements may be obtained on the basis of golf swings taken by a particular golfer outside of controlled testing conditions using the calibration ball, and a golfer-based linear relationship among the measurements may be determined for the calibration ball. The golfer-based linear relationship may also be expressed as a number normalized with respect to the baseline slope of the benchmark linear relationship for the calibration ball.

The baseline slope of the benchmark linear relationship may then be compared with the slope of the golfer-based linear relationship. On the basis of that comparison, and taking into account other golf shot parameters that may characterize golf shots taken by the golfer—for example, distance—as well as other factors including cost, one of the non-calibration balls may be recommended to complement or to maximize one or more parameters associated with the golfer's golf shots.

Methods such as those discussed above may also be executed by computer-based ball fitting systems, such as the systems disclosed in commonly owned U.S. Pat. No. 8,758,169, entitled "Method and System for Golf Ball Fitting Analysis," filed on Jul. 7, 2009, which is herein incorporated by reference, and the systems disclosed in copending and commonly owned U.S. Pat. Application Publication No. 20130190904, entitled "Method And System For Developing A Golf Ball Construction," filed on Jul. 26, 2012, which is herein incorporated by reference.

Such systems may include a computer, which may include, but is not limited to: a desktop computer, portable computer, tablet computer, smartphone, and/or any other device including a processor and/or a display that is configured to allow a user to view and/or interact with information. The computer may, in turn, include a CPU, a memory, a display, and a data transfer connection.

Computer-based ball fitting systems may include one or more automated measurement devices for obtaining measurements related to golf shot parameter values as well as a device for determining spin slopes and other relationships between golf shot parameter measurements. Such systems may also include a device to compare the spin slopes and linear relationships, and may include an output device, for example a printer or display, for providing a selection of a recommended golf ball between a plurality of golf balls on the basis of such comparisons. When executing methods such as those discussed above, these systems may (1) obtain measurements using the automated measurement devices, (2) use the determining device to determine spin slopes, (3) use the comparing device to compare the spin slopes, and (4) use the output device to provide a selection of a recommended golf ball between the golf balls.

While various embodiments of the invention have been described, the description is intended to be exemplary rather than limiting, and it will be apparent to those of ordinary skill in the art that many more embodiments and implementations are possible that are within the scope of the invention. Accordingly, the invention is not to be restricted except in light of the attached claims and their equivalents. Also, various modifications and changes may be made within the scope of the attached claims.

What is claimed is:

1. A method for providing a selection of a recommended golf ball, the method comprising steps of:

(i) obtaining (a) a first set of measurements for a first golf ball, including at least one ball spin measurement for each of a plurality of golf clubs having different club lofts, and (b) a second set of measurements for a second golf ball, including at least one ball spin measurement for each of the plurality of golf clubs;

(ii) determining (a) a first spin slope based upon the first set of measurements, and (b) a second spin slope based upon the second set of measurements; and (iii) providing a selection of a recommended golf ball between the first golf ball and the second golf ball;

wherein the recommended golf ball is the first golf ball if the first spin slope is larger than the second spin slope, and the recommended golf ball is the second golf ball if the first spin slope is not larger than the second spin slope.

2. The method of claim 1, wherein the first set of measurements is obtained by measuring strikes of the first golf ball, and the second set of measurements is obtained by measuring strikes of the second golf ball.

3. The method of claim 1, wherein a first club loft of the plurality of club lofts corresponds with a driver, and a second club loft of the plurality of club lofts corresponds with a wedge.

4. The method of claim 1, wherein one of the first set of measurements and the second set of measurements includes a composite measurement.

5. The method of claim 1, wherein one of the first spin slope and the second spin slope is based at least in part upon normalized differences between measurements.

6. The method of claim 1, wherein one of the first spin slope and the second spin slope is based at least in part upon normalized measurements.

7. The method of claim 1, wherein the first spin slope is based upon a line best fitting the first set of measurements and the second spin slope is based upon a line best fitting the second set of measurements.

8. The method of claim 1, wherein the first golf ball has a first configuration of a ball construction component, the second golf ball has a second configuration of the ball construction component, and the first configuration is different from the second configuration.

9. The method of claim 8, wherein the ball construction component is one of a number of pieces or layers, a golf ball cover material, a golf ball cover material hardness, a number of dimples in a golf ball cover, and a thickness of the golf ball cover.

10. A method for providing a selection of a recommended golf ball, the method comprising steps of:

(i) obtaining (a) a first set of ball spin measurements from a player making strikes with a first plurality of striking objects having different lofts, and (b) a second set of ball spin measurements from reference strikes made with a second plurality of striking objects having different lofts;

(ii) determining (a) a first linear relationship among the first set of ball spin measurements, and (b) a second linear relationship among the second set of ball spin measurements; and (iii) providing a selection of a recommended golf ball between a first golf ball and a second golf ball on the basis of at least the first linear relationship, the second linear relationship, and a spin slope criteria, wherein the configuration of a ball construction component of the second golf ball is different from the configuration of the ball construction component of the first golf ball.

11. The method of claim 10, wherein one of the first set (measurements and the second set of measurements includes a composite measurement.

12. The method of claim 10, wherein the second set of measurements is obtained through measurements of golf ball spin upon machine-based strikes.

13. The method of claim 10, wherein the second set of measurements is measured beforehand.

14. The method of claim 10, wherein one of the first plurality of striking objects and the second plurality of striking objects includes a plurality of golf clubs.

15. The method of claim 10, wherein a first striking object of the first plurality of striking objects is a driver, and a second striking object of the first plurality of striking objects is a wedge.

16. The method of claim 10, wherein the ball construction component is one of a number of pieces or layers, a golf ball cover material, a golf ball cover material hardness, a number of dimples in a golf ball cover, and a thickness of the golf ball cover.

17. The method of claim 10, wherein one of the first linear relationship and the second linear relationship is based at least in part upon normalized differences between measurements.

18. The method of claim 10, wherein one of the first linear relationship and the second linear relationship is based at least in part upon normalized measurements.

19. The method of claim 10, wherein the first linear relationship is based upon a line best fitting the first set of measurements.

20. The method of claim 10, wherein the spin slope criteria is which of the first linear relationship and the second linear relationship is the larger linear relationship, and wherein the recommended golf ball is the first golf ball if the first linear relationship is the larger linear relationship.

21. A method for providing a selection of a recommended golf ball, the method comprising steps of:

(i) obtaining (a) a first set of measurements for a first golf ball, including at least one ball spin measurement for each of a plurality of golf clubs that each having a different club loft, and (b) a second set of measurements for a second golf ball, including at least one ball spin measurement for each of the plurality of golf clubs;

(ii) determining (a) a first spin slope based upon the first set of measurements, and (b) a second spin slope based upon the second set of measurements; and (iii) providing a selection of a recommended golf ball between the first golf ball and the second golf ball;

wherein the recommended golf ball is selected based on a difference between the first spin slope and the second spin slope.

* * * * *